United States Patent
Yamato et al.

(10) Patent No.: US 9,157,924 B2
(45) Date of Patent: Oct. 13, 2015

(54) ANALYZING APPARATUS

(75) Inventors: Takashi Yamato, Kakogawa (JP); Hiroshi Kurono, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 585 days.

(21) Appl. No.: 12/870,494

(22) Filed: Aug. 27, 2010

(65) Prior Publication Data

US 2011/0053277 A1 Mar. 3, 2011

(30) Foreign Application Priority Data

Aug. 27, 2009 (JP) ................................. 2009-196460

(51) Int. Cl.
 *G01N 35/00* (2006.01)
 *G01N 35/10* (2006.01)
 G01N 35/04 (2006.01)

(52) U.S. Cl.
 CPC ........ *G01N 35/1004* (2013.01); *G01N 35/1002* (2013.01); *G01N 2035/00673* (2013.01); *G01N 2035/00801* (2013.01); *G01N 2035/0443* (2013.01); *Y10T 436/11* (2015.01); *Y10T 436/111666* (2015.01)

(58) Field of Classification Search
 None
 See application file for complete search history.

(56) References Cited

U.S. PATENT DOCUMENTS

| | | | |
|---|---|---|---|
| 5,827,479 A | 10/1998 | Yamazaki et al. | |
| 6,090,630 A | 7/2000 | Koakutsu et al. | |
| 7,931,863 B2 | 4/2011 | Kitagawa et al. | |
| 2006/0178776 A1* | 8/2006 | Feingold et al. | ............. 700/245 |
| 2008/0011106 A1 | 1/2008 | Kitagawa et al. | |
| 2008/0014118 A1 | 1/2008 | Kitagawa et al. | |

FOREIGN PATENT DOCUMENTS

| | | |
|---|---|---|
| CN | 101097222 | 1/2008 |
| EP | 0411620 A2 | 8/1990 |
| JP | 03-065654 | 3/1991 |
| JP | 09-196925 | 7/1997 |
| JP | 2001-91522 A | 4/2001 |
| JP | 2008-032670 | 2/2008 |
| JP | 2008-122417 A | 5/2008 |
| JP | 2008-190959 A | 8/2008 |
| JP | 2008-216173 A | 9/2008 |

\* cited by examiner

*Primary Examiner* — Yelena G Gakh
*Assistant Examiner* — Michelle Adams
(74) *Attorney, Agent, or Firm* — Sughrue Mion, PLLC

(57) ABSTRACT

A specimen analyzing apparatus for measuring a specimen by using a reagent which has a dispensing mechanism which includes a dispensing tube for suctioning and discharging liquid; a reagent container holder from which a reagent container is removable when the reagent container is in a container removal area; a receiving section for receiving a replacement command for a replacement of the reagent; and a controller for controlling the dispensing mechanism so as to retreat the dispensing tube from the container removal area when the replacement command has been received by the receiving section. Also, a control method for a specimen analyzing apparatus.

23 Claims, 11 Drawing Sheets

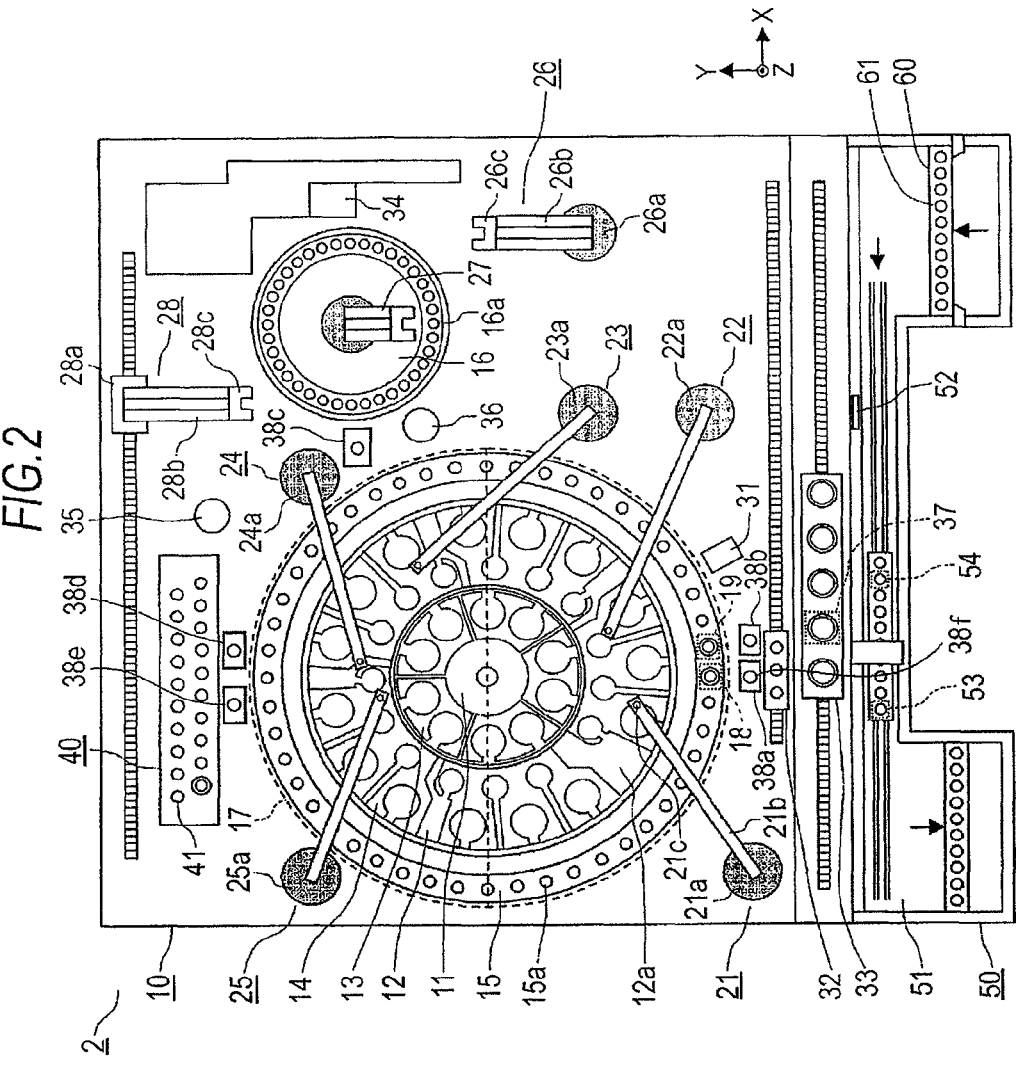

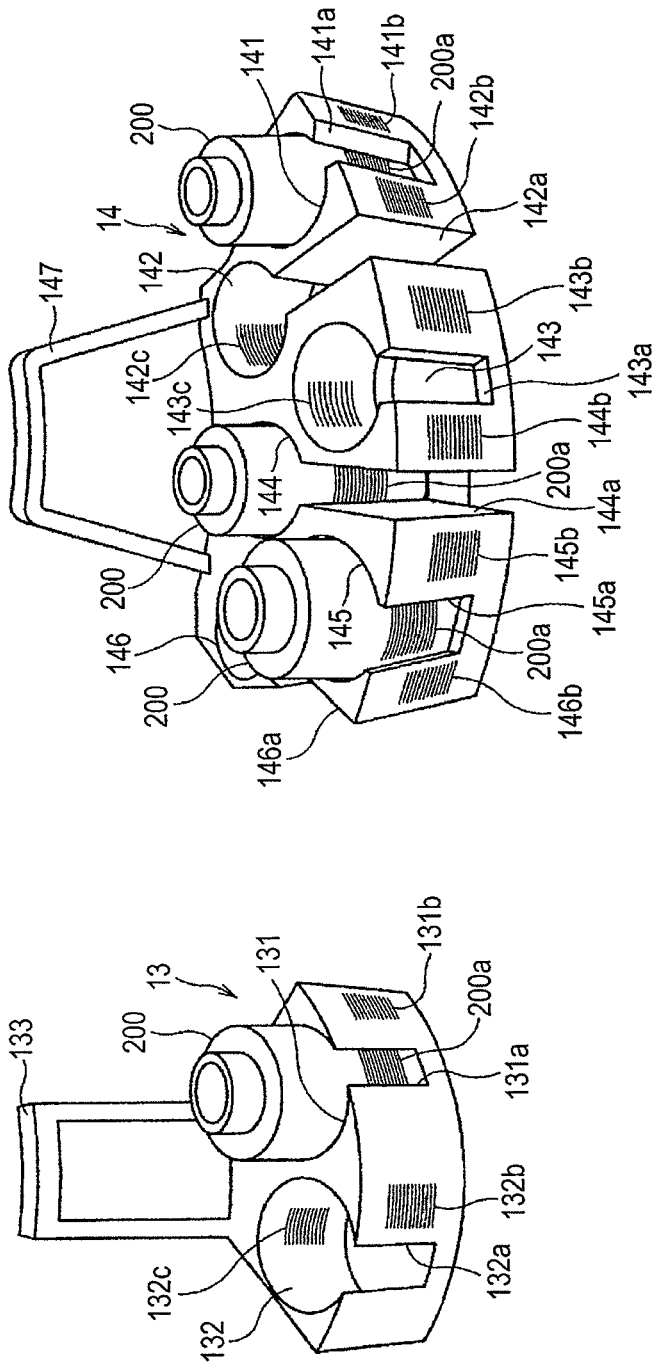

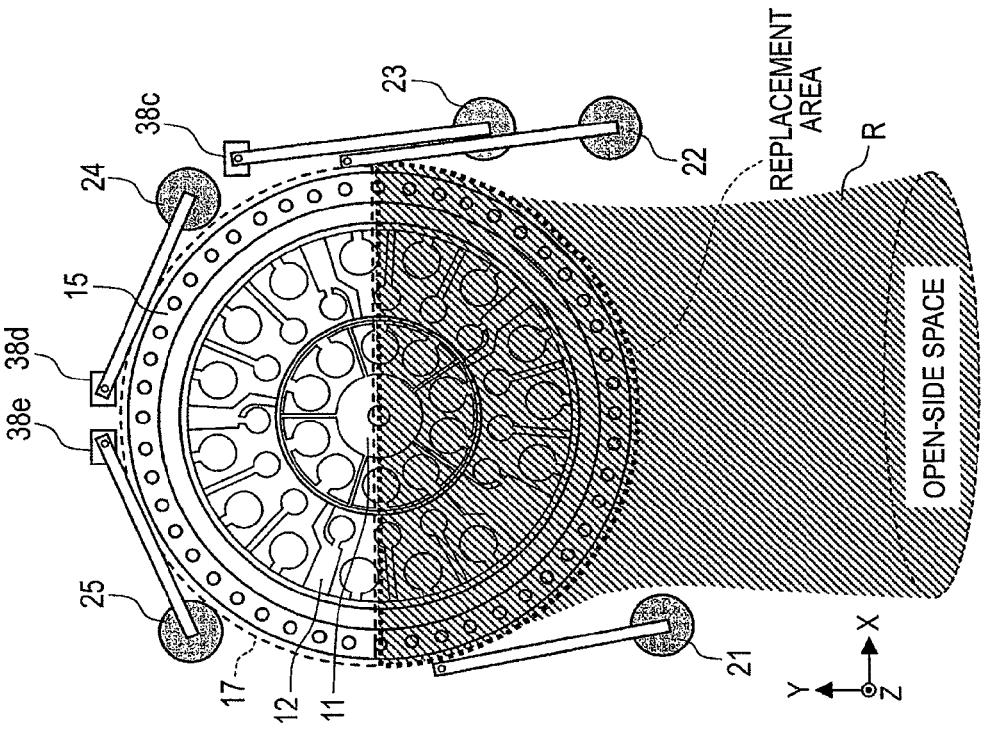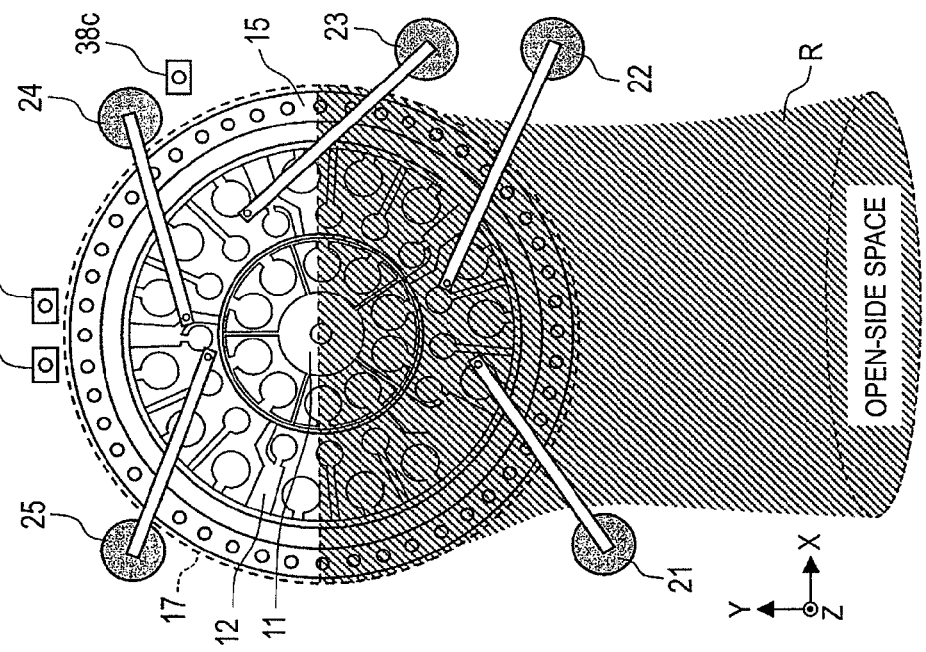

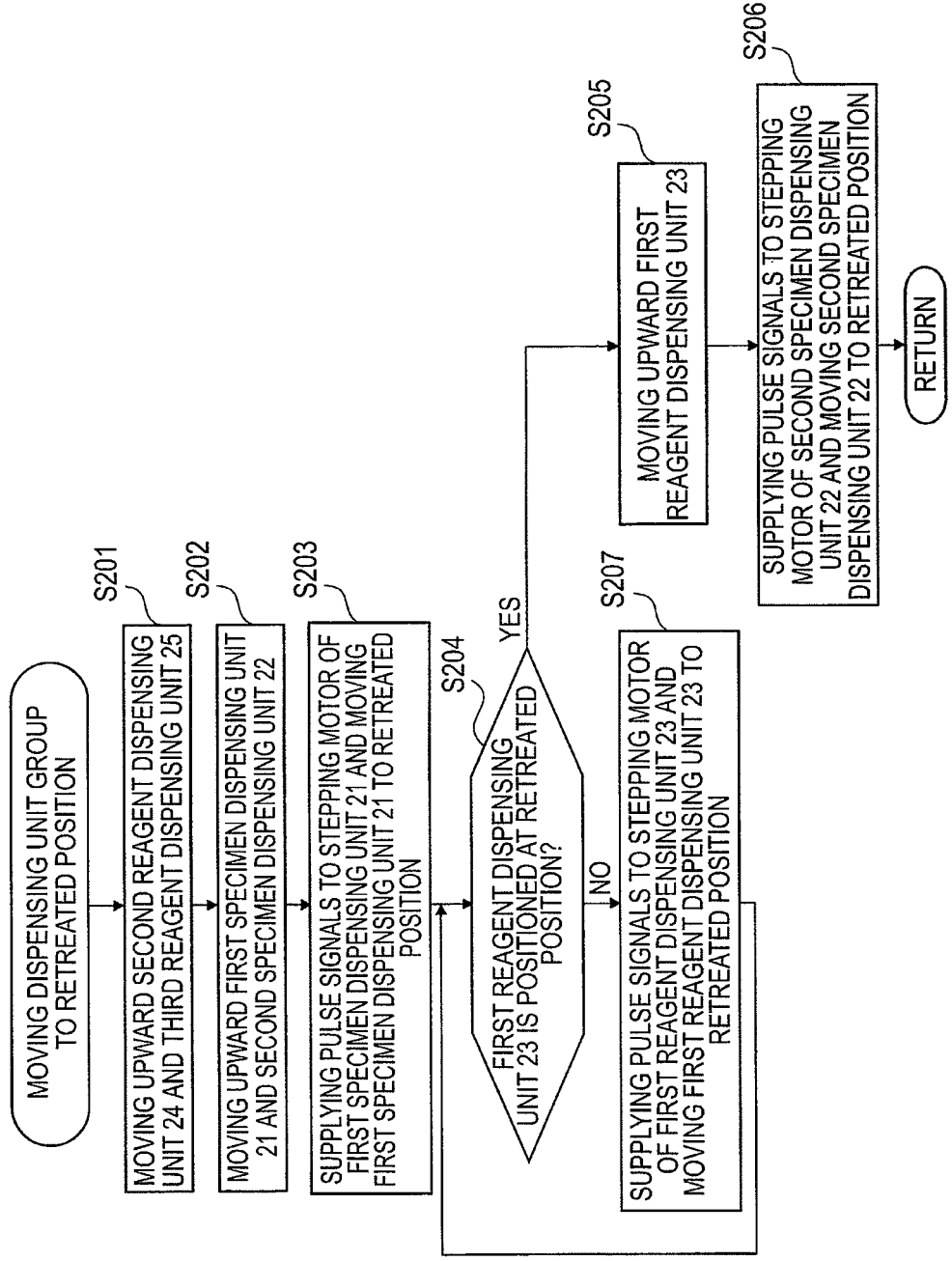

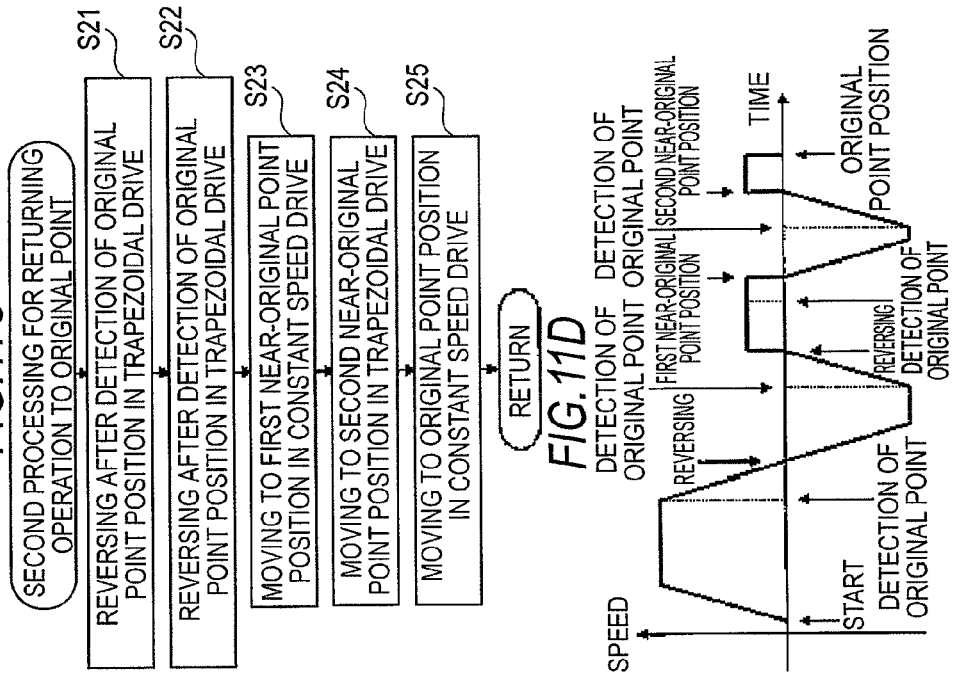

ANALYZING APPARATUS

CROSS REFERENCE TO RELATED APPLICATION

This application claims priority from Japanese Patent Application No. 2009-196460, filed on Aug. 27, 2009, in the Japanese Patent Office.

FIELD OF THE INVENTION

The present invention relates to a specimen analyzing apparatus for performing a measurement process on a specimen and a control method for the same.

BACKGROUND

Conventionally, a specimen analyzing apparatus for measuring a specimen by using a reagent has been known. According to such a specimen analyzing apparatus, a measurement sample prepared by mixing a specimen and a reagent is measured by a measurement section. When such preparation is performed, the specimen and the reagent are suctioned and dispensed by a corresponding pipette or the like, respectively. The reagent is contained in a reagent container and set in the specimen analyzing apparatus. When an amount of the reagent contained in the reagent container gets smaller, a user replaces the reagent container.

For example, in a specimen analyzing apparatus described in U.S. Patent Publication No. 2008/0014118, by mounting a container rack holding a reagent container on a reagent table, the reagent container is set in the specimen analyzing apparatus. In this case, the replacement of a reagent container can be realized by employing the configuration in which a container rack holding a reagent container to be replaced is positioned at a container replacement position which can be opened to the outside.

In this configuration, the reagent table is driven in response to a user's command for the replacement of the reagent to transport and the container rack for holding a reagent container as a replacement target is transported to the container replacement position. A user takes out the container rack positioned at the container replacement position and the user replaces the reagent container as a replacement target with a reagent container containing a new reagent. Then, the user mounts the container rack holding the new reagent container on the reagent table. In this manner, the replacement of the reagent is completed.

However, in the above-described configuration, in order to prevent a user from coming into contact with a pipette of a dispensing mechanism during the replacement of the reagent, it is necessary to move the pipette of the dispensing mechanism so as not to come within the range of the container replacement position. Accordingly, the degree of freedom in the layout of the dispensing mechanism is limited by the container replacement position.

SUMMARY OF THE INVENTION

According to a first aspect of the present invention, a specimen analyzing apparatus for measuring a specimen by using a reagent includes a dispensing mechanism which includes a dispensing tube for suctioning and discharging liquid; a reagent container holder from which a reagent container is removable when the reagent container being in a container removal area; a receiving section for receiving a replacement command for a replacement of the reagent; and a controller for controlling the dispensing mechanism so as to retreat the dispensing tube from the container removal area when the replacement command has been received by the receiving section.

According to a second aspect of the present invention, a specimen analyzing apparatus for measuring a specimen by using a reagent has a dispensing mechanism which includes a dispensing tube for suctioning and discharging liquid; a reagent container holder from which a reagent container is removable when the reagent container being in a container removal area; a remaining amount detection section for detecting a remaining amount of the reagent in the reagent container held in the reagent container holder; and a controller for controlling the dispensing mechanism so as to retreat the dispensing tube from the container removal area when it is determined that the remaining amount of the reagent in the reagent container held in the reagent container holder is insufficient on the basis of the detection result of the remaining amount detection section.

According to a third aspect of the present invention, a specimen analyzing apparatus for measuring a specimen by using a reagent has a dispensing mechanism which includes a dispensing tube for suctioning and discharging liquid; a reagent container holder in which a reagent can be added when the reagent container being in a reagent adding area; a receiving section for receiving an addition command for an addition of the reagent; and a controller for controlling the dispensing mechanism so as to retreat the dispensing tube from the reagent adding area when the receiving section receives the addition command.

According to a fourth aspect of the present invention, a control method for a specimen analyzing apparatus which includes a dispensing tube for suctioning and discharging liquid and a reagent container holder includes receiving a replacement command for a replacement of a reagent; and retreating the dispensing tube from a container removal area in which a reagent container is removable from the reagent container holder, based on the replacement command.

BRIEF DESCRIPTION OF THE DRAWINGS

FIG. 2 is a plan view showing a schematic configuration of the inside of a measurement apparatus according to an embodiment.

FIG. 3A is a diagram showing a configuration of a container rack according to an embodiment.

FIG. 3B is a diagram showing a configuration of a container rack according to an embodiment.

FIG. 4A is a diagram illustrating a procedure for a replacement or an addition of a reagent according to an embodiment.

FIG. 4B is a diagram illustrating a procedure for a replacement or an addition of a reagent according to an embodiment.

FIG. 10 is a flow chart showing a process of moving a dispensing unit to a retreated position according to an embodiment.

FIG. 11A is a diagram illustrating a processing content of a processing for a returning operation to an original point according to an embodiment.

FIG. 11B is a diagram illustrating a processing content of a processing for a returning operation to an original point according to an embodiment.

FIG. 11C is a diagram illustrating a processing content of a processing for a returning operation to an original point according to an embodiment.

FIG. 11D is a diagram illustrating a processing content of a processing for a returning operation to an original point according to an embodiment.

DETAILED DESCRIPTION OF THE PREFERRED EMBODIMENTS

Hereinafter, embodiments of the specimen analyzing apparatus are described with reference to the drawings.

Figure 1:
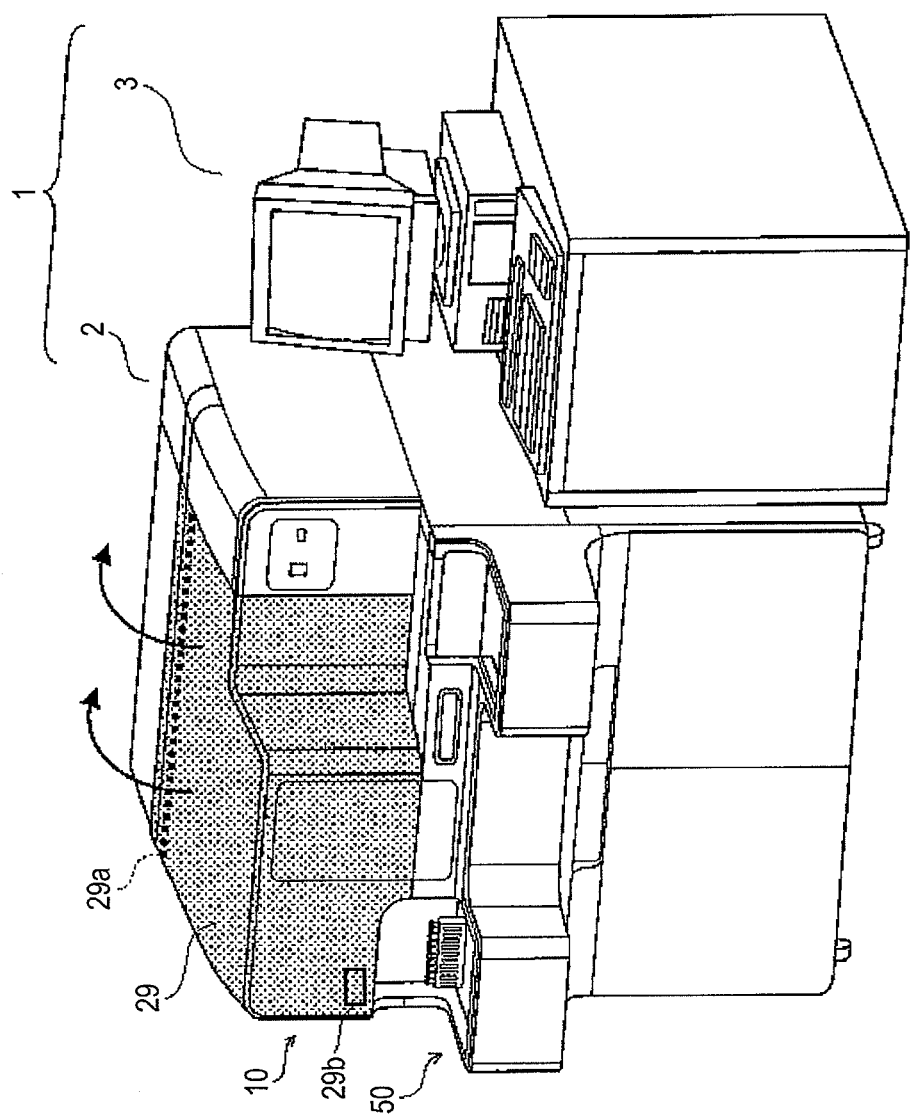
FIG. 1 is a diagram showing a configuration of a specimen analyzing apparatus according to an embodiment.

FIG. 1 is a diagram showing a configuration of a specimen analyzing apparatus 1 according to the present embodiment. The specimen analyzing apparatus 1 is a blood coagulation analyzing apparatus which performs light irradiation on a sample for measurement, which has been prepared by adding a reagent to a specimen (plasma), and optically measures and analyzes the specimen by using a coagulation method, a synthetic substrate method, an immunoturbidimetric method and a condensation method. The specimen analyzing apparatus 1 includes a measurement apparatus 2 for optically measuring components included in a specimen (plasma), and an information processing apparatus 3 for analyzing measurement data of the measurement apparatus 2 and providing an operation command to the measurement apparatus 2.

FIG. 2 is a plan view showing a schematic configuration of the inside of the measurement apparatus 2 when seen from an upper direction. The measurement apparatus 2 includes a measurement unit 10, a detection unit 40, and a transport unit 50. In this drawing, a coordinate axis indicating the position is additionally shown.

The measurement unit 10 includes a first reagent table 11, a second reagent table 12, a first container rack 13, a second container rack 14, a cuvette table 15, a warming table 16, a table cover 17, a first specimen dispensing unit 21 which includes a first dispensing tube, a second specimen dispensing unit 22 which includes a second dispensing tube, a first reagent dispensing unit 23, a second reagent dispensing unit 24, a third reagent dispensing unit 25, a first catcher unit 26, a second catcher unit 27, a third catcher unit 28, a reagent bar-code reader 31, a cuvette transporter 32, a diluent transporter 33, a cuvette port 34, a waste port 35, a waste port 36 and pipette cleaners 38a to 38e. The measurement unit 10 further includes a main body cover 29 (see FIG. 1) for covering the inside.

The first reagent table 11, the second reagent table 12, the cuvette table 15, and the warming table 16 are circular tables, each of which is independently rotated and driven in both clockwise and counterclockwise directions. These tables are rotated and driven respectively by stepping motors 311a, 311b, 313, and 314 (see FIG. 5) arranged on the rear sides of the lower surfaces.

As shown in FIG. 2, the five first container racks 13 and the five second container racks 14 are detachably arranged on the upper surfaces of the first reagent table 11 and the second reagent table 12, respectively. In the first container racks 13 and the second container racks 14, holding sections for holding reagent containers are formed. The reagent bar-code reader 31 is positioned outside the second reagent table, and the first reagent table 11 is positioned inside the second reagent table 12.

In addition, as shown in FIG. 2, when the five second container racks 14 are arranged in the second reagent table 12, a gap 12a from among the gaps between adjacent second container racks 14 has larger clearance as compared with the other gaps. With this configuration, the reagent bar-code reader 31 can read bar-code information on the first container racks 13 arranged in the first reagent table 11 and on the reagent containers contained therein, via the gap 12a with a larger clearance compared with the other gaps.

Here, a description will be made of the configurations of the first container rack 13 and the second container rack 14 and the procedure in which the bar-code information attached to these container racks is obtained, with reference to the perspective views shown in FIGS. 3A and 3B.

Referring to FIG. 3A, the first container rack 13 includes two holding sections 131 and 132 for holding cylindrical reagent containers 200, notch sections 131a and 132a which are respectively provided in the front surfaces of the holding sections 131 and 132, and a gripped portion 133 which is provided so as to upwardly protrude. The holding sections 131 and 132 have containable parts with substantially circular shapes when seen from an upper direction so as to hold the reagent containers 200. In addition, when holding a container with a smaller outer shape as compared with the inner diameters of the holding sections 131 and 132, the first container rack 13 stably holds such a container using an additional adapter or the like.

Bar-code labels 131b and 132b are attached to the outer circumferential surfaces of the holding sections 131 and 132, respectively. In addition, bar-code labels are also attached to the inner circumferential surfaces of the holding sections 131 and 132, respectively. A bar-code label 200a is attached to the reagent container 200. FIG. 3A shows only the bar-code label 132c attached to the inner circumferential surface of the holding section 132 from among the bar-codes attached to the inner circumferential surfaces of the holding sections 131 and 132.

As shown in FIG. 3B, the second container rack 14 includes six holding sections 141 to 146 for holding cylindrical reagent containers 200, notch sections 141a to 146a which are respectively provided in the front surfaces of the holding sections 141 to 146, and a gripped portion 147 which is provided so as to upwardly protrude. The holding sections 141 to 146 have containable parts with substantially circular shapes when seen from an upper direction so as to hold the reagent containers 200. In addition, when holding a container with a smaller outer shape as compared with the inner diameters of the holding sections 141 to 146, the second container rack 14 stably holds such a container using an additional adapter or the like.

Bar-code labels 141b to 146b are attached to the outer circumferential surfaces of the holding sections 141 to 146, respectively. Bar-code labels are also attached to the inner circumferential surfaces of the holding sections 141 to 146, respectively. A bar-code label 200a is attached to the reagent container 200. FIG. 3B shows only the bar-code labels 142c and 143c attached to the inner circumferential surface of the holding sections 142 and 143 from among the bar-code labels attached to the inner circumferential surfaces of the holding sections 141 to 146.

Next, a description will be made of the procedure in which the bar-code labels attached to the first container rack 13, the second container rack 14, and the reagent container 200 are read. In addition, the reagent bar-code reader 31 reads the bar-code labels from the front direction in FIGS. 3A and 3B.

First, the first reagent table and the second reagent table are rotated at a predetermined speed in a predetermined direction, and the bar-code labels attached to the outer circumferential surface of a predetermined holding section is read by the bar-code reader 31. With this operation, it is recognized that this holding section corresponds to which holding section in which container rack.

Subsequently, the bar-code positioned in the notch section of this holding section is read. At this time, the bar-code label attached to the reagent container 200 is read when the reagent container 200 is contained, and the bar-code label attached to the inner circumferential surface of the holding section is read when the reagent container 200 is not contained. In this manner, it is determined whether or not the reagent container 200 is contained in the holding section. Moreover, when the reagent container 200 is contained in the holding section, the type of the reagent contained in the reagent container 200 is identified based on the bar-code information read from the bar-code label 200a.

As shown in FIG. 2, a plurality of cuvette holding holes 15a and 16a are formed respectively in the cuvette table 15 and the warming table 16 along their circumference. When the cuvettes are set in the cuvette holding holes 15a and 16a, these cuvettes are moved in the circumferential positions along with the rotations of the cuvette table 15 and the warming table 16. In addition, the warming table 16 warms the cuvettes set in the holding holes 16a at a predetermined temperature.

The table cover 17 is provided so as to cover the upper surfaces of the first reagent table 11, the second reagent table 12, and the cuvette table 15. The table cover 17 has a folding mechanism in its center portion such that only the front half thereof (Y-axis negative direction) can be opened. In addition, the table cover 17 is provided with a plurality of holes. Dispensing by the first specimen dispensing unit 21, the second specimen dispensing unit 22, the first reagent dispensing unit 23, the second reagent dispensing unit 24, and the third reagent dispensing unit 25 is performed through this plurality of holes.

The first specimen dispensing unit 21 includes a supporting section 21a, an arm 21b, and a dispensing section 21c as shown in FIG. 2. The supporting section 21a is rotated and driven by a stepping motor 312a (see FIG. 5) arranged on the rear side of the lower surface. The supporting section 21a supports the arm 21b, and the arm 21b is driven in the vertical direction (Z-axis direction) by the stepping motor 312a. The dispensing section 21c is attached to a leading end of the arm 21b, and has a pipette (a dispensing tube). This pipette is used to suction and discharge the specimen.

When the supporting section 21a is rotated and driven, the dispensing section 21c is moved on a circumference around the supporting section 21a. The dispensing section 21c suctions the specimen, which exists directly below the dispensing section 21c, in the specimen suctioning position, and discharges the specimen into the cuvette, which exists directly below the dispensing section 21c, in the specimen discharging position.

The first specimen dispensing unit 21 has a tube for supplying cleaning liquid to the pipette of the dispensing section 21c. Such a tube is disposed so as to reach the upper portion of the pipette of the dispensing section 21c from the supporting section 21a along the arm 21b. The cleaning liquid is supplied to the inside of the pipette from the side of the supporting section 21a via the tube.

In addition, the second specimen dispensing unit 22, the first reagent dispensing unit 23, the second reagent dispensing unit 24, and the third reagent dispensing unit 25 have the same configuration as that of the first specimen dispensing unit 21. That is, the second specimen discharging unit 22 is provided with a supporting section 22a, and the supporting section 22a is rotated and driven by a stepping motor 312b (see FIG. 5) arranged on the rear side of the lower surface. In addition, the first reagent dispensing unit 23, the second reagent dispensing unit 24, and the third reagent dispensing unit 25 are provided with a supporting section 23a, a supporting section 24a, and a supporting section 25a, respectively. Moreover, the supporting section 23a, the supporting section 24a, and the supporting section 25a are rotated and driven by a stepping motor 312c, a stepping motor 312d, and a stepping motor 312e (see FIG. 5) arranged on the rear sides of the lower surfaces, respectively.

The rotation driving ranges of the first specimen dispensing unit 21 and the third reagent dispensing unit 25 do not overlap with the rotation driving ranges of other dispensing units. In addition, the second reagent dispensing unit 24 is rotated and driven in a range not overlapping with the rotation driving ranges of the second specimen dispensing unit 22 and the first reagent dispensing unit 23. The first specimen dispensing unit 22 and the first reagent dispensing unit 23 are controlled in rotation driving so as not to overlap with each other.

The first catcher unit 26 includes a supporting section 26a for supporting an arm 26b, the arm 26b which can be extended and contracted, and a gripping section 26c as shown in FIG. 2. The supporting section 26a is rotated and driven by a stepping motor 315a (see FIG. 5) arranged on the rear side of the lower surface. The gripping section 26c is attached to the leading end of the arm 26b, and can grip the cuvette. In addition, the second catcher unit 27 has the same configuration as that of the first catcher unit 26, and is rotated and driven by a stepping motor 315b disposed in a rear side of the lower surface (see FIG. 5).

The third catcher unit 28 includes a supporting section 28a for supporting an arm 28b, the arm 28b which can be extended and contracted, and a gripping section 28c which is attached to the leading end of the arm 28b as shown in FIG. 2. The supporting section 28a is driven along a rail arranged in a horizontal direction (X-axis direction). The gripping section 28c can grip the cuvette.

The reagent bar-code reader 31 reads a bar-code label attached to the first container rack 13 and the second container rack 14, and bar-code labels 200a attached to the reagent containers 200 contained in these racks. In addition, the first reagent table 11 and the second reagent table 12 can be independently rotated. The bar-code label attached to the first container rack 13 and the bar-code labels 200a attached to the reagent containers 200 contained in the first container rack 13 are read via the gap 12a when the gap 12a of the second reagent table 12 reaches the position in front of the reagent bar-code reader 31.

The cuvette transporter 32 and the diluent transporter 33 are driven on the rails in the horizontal direction (X-axis direction). In addition, holes for holding the cuvettes and the diluent containers are provided in the cuvette transporter 32 and the diluent transporter 33, respectively.

The cuvette port 34 is always supplied with new cuvettes. The new cuvettes are set in the holes of the cuvette transporter 32 for holding the cuvettes and in the cuvette holding hole 15a of the cuvette table 15 by the first catcher unit 26 and the second catcher unit 27. The waste ports 35 and 36 are the holes for disposing of the unnecessary cuvettes after the completion of the analysis.

The pipette cleaners 38a to 38e (more generally, cleaning sections) are used when cleaning the pipettes of the first specimen dispensing unit 21, the second specimen dispensing unit 22, the first reagent dispensing unit 23, the second reagent dispensing unit 24 and the third reagent dispensing unit 25, respectively. In the pipette cleaners 38a to 38e, holes (more generally, opening sections), such as for example hole 38f, for cleaning the pipettes are formed in a vertical direction (Z-axis direction). When the pipettes are contained in the holes, the pipette cleaners 38a to 38e fill the holes with cleaning liquid to clean the outside of the pipettes.

The main body cover 29 shown in FIG. 1 is configured so as to turn around a rotation axis 29a, thereby opening the measurement unit 10. In general, during the measurement operation of the measurement unit 10, the main body cover 29 covers the mechanisms in the measurement unit 10, such as the first reagent table 11, the second reagent table 12, the first specimen dispensing unit 21, the second specimen dispensing unit 22, the first reagent dispensing unit 23, the second reagent dispensing unit 24 and the third reagent dispensing unit 25. The main body cover 29 includes a lock mechanism section 29b. When covering the mechanisms in the measurement unit 10, the opening of the cover can be prevented by the lock mechanism section 29b. When the measurement operation of the measurement unit 10 is suspended and a reagent container is replaced, the main body cover 29 is opened and the reagent container can be taken out of the reagent table.

The detection unit 40 is provided with twenty holding holes 41 for containing cuvettes in the upper surface thereof, and a detection section on the rear side of the lower surface thereof. When the cuvettes are set in the holding holes 41, optical information, reflecting components included in the sample for measurement in the cuvette, is detected by the detection section. For example, the detection unit 40 performs optical irradiation on the sample for measurement, thereby detecting as a variation in transmitted light a variation in turbidity when fibrinogen in the sample for measurement is converted into fibrin.

The transport unit 50 is provided with a transport passage 51 and a specimen bar-code reader 52. The bottom surface of the transport passage 51 includes a right tank area on its right side, a connecting area in its center, and a left tank area on its left side, and is formed in a U-shape. The specimen bar-code reader 52 reads bar-code labels attached to the specimen containers 61 contained in the specimen rack 60 which is transported through the connecting area.

Next, a description will be made of a series of operations for analyzing the specimen.

First, the specimen rack 60 containing a plurality of specimen containers 61 is set in the right tank area (area in an X-axis positive direction) of the transport passage 51. The specimen rack 60 is moved backward (Y-axis positive direction) in the right tank area, and then moved in the left direction (X-axis negative direction) through the connecting area. At this time, the bar-code labels attached to the specimen containers 61 are read by the specimen bar-code reader 52. Subsequently, the specimen rack 60 is positioned in a predetermined position in the connecting area. When the suctioning of the specimen is completed in the connecting area, the specimen rack 60 is moved in the left direction (X-axis negative direction) through the connecting area, and then moved forward (Y-axis negative direction) in the left tank area (area in the X-axis negative direction).

The first specimen dispensing unit 21 suctions the specimen in the specimen container 61 which is positioned at a predetermined specimen suctioning position 53 in the connecting area of the transport passage 51. The specimen suctioned by the first specimen dispensing unit 21 is discharged into the cuvette set in the cuvette holding hole 15a positioned in a specimen discharging position 18 (Y-axis negative direction) in front of the cuvette table 15.

The second specimen dispensing unit 22 suctions the specimen contained in the cuvette in the specimen suctioning position 19 (Y-axis negative direction) in front of the cuvette table 15, or the specimen in the specimen container 61 positioned at a predetermined specimen suctioning position 54 in the connecting area of the transport passage 51. The specimen suctioned by the second specimen dispensing unit 22 is discharged into the cuvette set in the cuvette transporter 32. In addition, the second specimen dispensing unit 22 can suction the diluent set in the diluent transporter 33. In this case, the second specimen dispensing unit 22 suctions the diluent at a diluent suctioning position 37 before the suctioning of the specimen, and then suctions the specimen at the specimen suctioning position 19 or 54.

The first specimen dispensing unit 21 and the second specimen dispensing unit 22 are rotated and driven such that the pipettes are positioned just above (original point positions) the pipette cleaners 38a and 38b, respectively, when the dispensing ends. Thereafter, these dispensing units are driven downward (Z-axis negative direction) such that the pipettes are contained in the holes of the pipette cleaners 38a and 38b. In this manner, the first specimen dispensing unit 21 and the second specimen dispensing unit 22 enters a standby state.

In addition, the pipettes of the first specimen dispensing unit 21 and the second specimen dispensing unit 22 are contained in the pipette cleaners 38a and 38b after every dispensing of the specimen such that the inside and outside of the pipettes are cleaned. The inside of the pipette is cleaned by supplying cleaning liquid to the inside of the pipette via the tube disposed in the dispensing unit, as described above. The cleaning liquid used in the cleaning is disposed of in the pipette cleaner. The outside of the pipette is cleaned by filling the pipette cleaner with cleaning liquid, as described above.

The cuvette transporter 32 is driven on the rail in the right direction (X-axis positive direction) at a predetermined timing, when the specimen is discharged into the cuvette contained therein. Subsequently, the cuvette, which contains the specimen, set in the cuvette transporter 32 is gripped by the first catcher unit 26, and set in the cuvette holding hole 16a of the warming table 16.

Subsequently, the second catcher unit 27 grips the cuvette, which contains the specimen, set in the holding hole 16a, and moves it to an area just above the pipette cleaner 38c. Here, the first reagent dispensing unit 23 suctions a reagent (a first reagent) within a predetermined reagent container 200 positioned in the first reagent table 11 or in the second reagent table 12, and discharges the reagent at the area just above the pipette cleaner 38c. Accordingly, when the reagent is discharged, the second catcher unit 27 stirs this cuvette, and sets it in the cuvette holding hole 16a of the warming table again.

The cuvette held by the cuvette holding hole 16a of the warming table 16 is then gripped by the third catcher unit 28, and positioned at an area just above the pipette cleaner 38d or the pipette cleaner 38e. Here, the second reagent dispensing unit 24 and the third reagent dispensing unit 25 suction a reagent (a second reagent) in a predetermined reagent container 200 positioned in the first reagent table 11 or in the second reagent table 12, and discharge it at the areas just above the pipette cleaners 38d and 38e, respectively. When the reagent is discharged in this manner, the third catcher unit 28 sets the cuvette, into which the reagent is discharged, in the holding hole 41 of the detection unit 40. Thereafter, optical information is detected from the sample for measurement, which is contained in the cuvette, in the detection unit 40.

As in the first specimen dispensing unit 21 and the second specimen dispensing unit 22, the pipettes of the first reagent dispensing unit 23, the second reagent dispensing unit 24 and the third reagent dispensing unit 25 are positioned just above (original point positions) the pipette cleaners 38c, 38d and 38e, respectively, when the dispensing ends. After that, these pipettes are contained in the pipette cleaners 38c, 38d and 38e and enter a standby state. In addition, these pipettes of the dispensing units are also cleaned after every dispensing of different reagents in accordance with the same procedure as that for the cleaning of the pipettes of the first specimen dispensing unit 21 and the second specimen dispensing unit 22.

Although both of the mixing of the reagent (first reagent) by the first reagent dispensing unit 23 and the mixing of the reagent (second reagent) by the second reagent dispensing unit 24 and the third reagent dispensing unit 25 were performed here, mixing of the first reagent may not be performed in some cases depending upon the contents of the analysis. In such a case, the mixing step of the first reagent is skipped, and the optical information is detected after only the mixing of the second reagent is performed.

The unnecessary cuvette after the completion of the detection by the detection unit 40 is moved up to the position directly above the waste port 35 while being gripped by the third catcher unit 28, and disposed of in the waste port 35. In addition, the cuvette held in the cuvette holding hole 15a of the cuvette table 15 is also positioned at a place close to the second catcher unit 27 by rotating the cuvette table 15, when it becomes unnecessary after the completion of the analysis. The second catcher unit 27 grips the unnecessary cuvette held in the cuvette holding hole 15a, and disposes of it in the waste port 36.

When the disposal of the cuvette is performed by the second catcher unit 27, the first reagent dispensing unit 23 is evaded from the route of the disposal of the cuvette so as not to disturb the cuvette disposal of the second catcher unit 27. For example, when the pipette of the first reagent dispensing unit 23 is contained in the pipette cleaner 38c (standby state), the first reagent dispensing unit 23 is timely lifted from the pipette cleaner 38c and rotated and driven so as not to disturb the cuvette disposal of the second catcher unit 27.

FIGS. 4A and 4B are drawings illustrating a procedure for a replacement or an addition of a reagent during the suspension of the measurement operation. FIG. 4A is a diagram showing a state in which a specimen or a reagent is dispensed and FIG. 4B is a diagram showing a state in which a reagent is replaced or added during the suspension of the measurement operation.

As shown in FIG. 4A, in a state in which a specimen or a reagent is dispensed, the table cover 17 covers the upper surfaces of the first reagent table 11, the second reagent table 12 (hereinafter, referred to as a "reagent table group"), and the cuvette table 15. At this time, the first specimen dispensing unit 21, the second specimen dispensing unit 22, the first reagent dispensing unit 23, the second reagent dispensing unit 24 and the third reagent dispensing unit 25 (hereinafter, referred to as a "dispensing unit group") perform the dispensing via a plurality of the holes provided in the table cover 17.

As shown in FIG. 4B, when replacing or adding a reagent during the suspension of the measurement operation, the dispensing unit group is rotated and driven up to a position (hereinafter, referred to as a "retreated position") outside an area which is covered by the table cover 17. Thereafter, the table cover 17 is folded at its center portion. With this operation, the state changes to the one in which only the back half area (Y-axis positive direction) of the reagent table group and the cuvette table 15 is covered with the table cover 17 as shown in FIG. 4B. The part surrounded by a broken line represents the area which is covered with the table cover 17 and the part surrounded by a dashed line represents the area which is not covered with the table cover 17.

At this time, since an area (hereinafter, referred to as a "replacement area") which is not covered with the table cover 17 is formed in the front half area (Y-axis negative direction) of the reagent table group, a user can replace or add the reagent through such a replacement area. That is, the user takes out the first reagent rack 13 and the second reagent rack 14 through the replacement area, replaces or adds the reagent, and then sets the reagent racks to the reagent tables again. Alternatively, the user directly replaces or adds the reagent with respect to the reagent containers 200 arranged in the reagent racks.

In this embodiment, the retreated positions of the dispensing unit group mean that the dispensing units are rotated and driven in the X-Y plane and positioned at rotation positions shown in FIG. 4B, respectively. In this state, the positions of the pipettes of the first reagent dispensing unit 23, the second reagent dispensing unit 24 and the third reagent dispensing unit 25 in the dispensing unit group in the X-Y plane are the same as the positions of the respective corresponding pipette cleaners in the X-Y plane.

The retreated positions of the dispensing units according to the present invention are not limited to the retreated positions shown in FIG. 4B, and the dispensing units may be positioned anywhere if they are away from a replacement route R, from an open-side space (a space where the user insert their hand by opening the main body cover 29) shown in FIG. 4B to a space above the above-described replacement area, for replacing the reagent container by a user. Accordingly, for example, the second reagent dispensing unit 24 and the third reagent dispensing unit 25 may be retreated to the upper space of the table cover 17 with the exception of the upper space of the replacement area.

Figure 5:
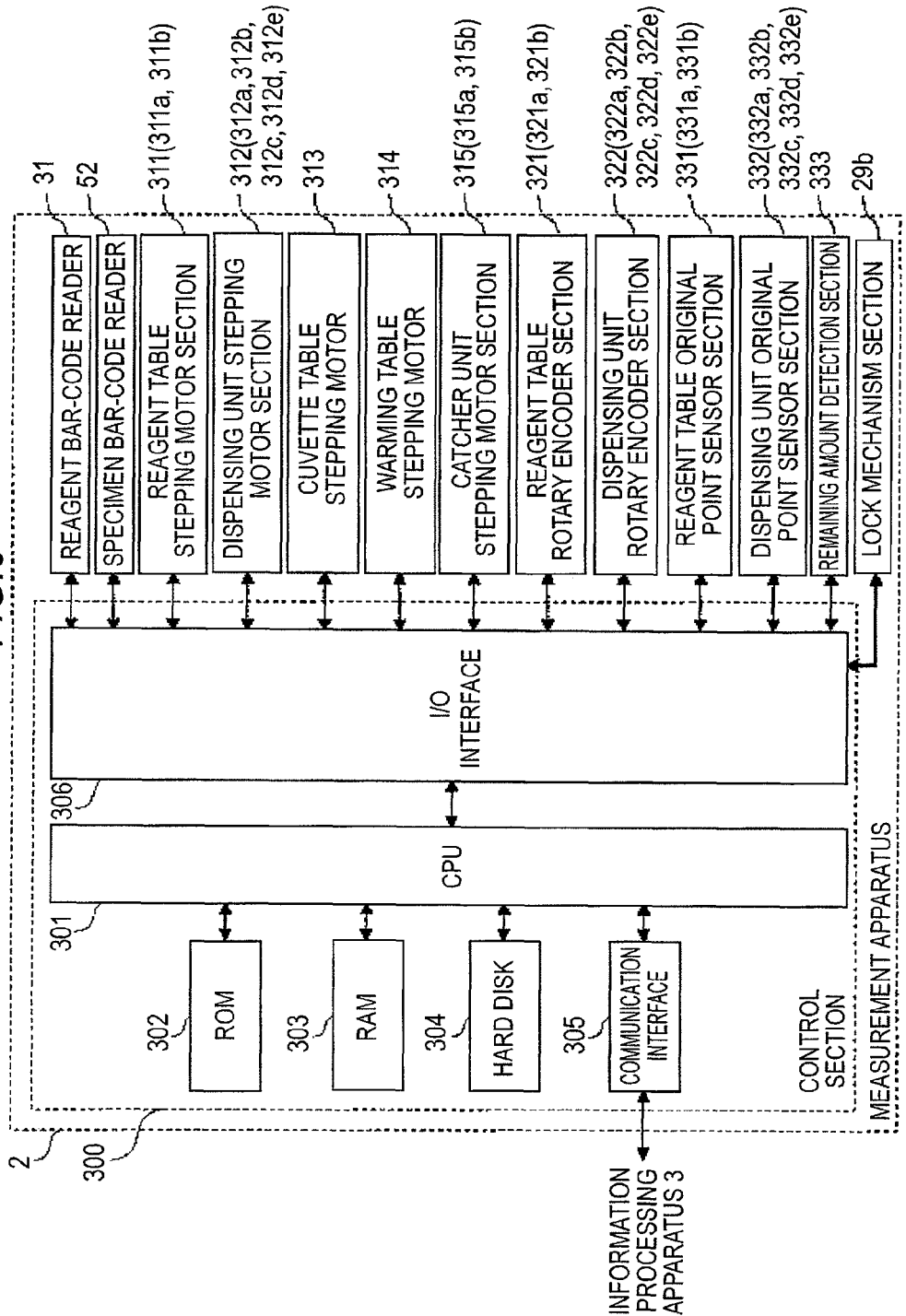
FIG. 5 is a diagram showing a circuit configuration of a measurement apparatus according to an embodiment.

FIG. 5 is a diagram showing a circuit configuration of the measurement apparatus 2.

The measurement apparatus 2 includes a control section 300, a reagent bar-code reader 31, a specimen bar-code reader 52, a reagent table stepping motor section 311, a dispensing unit stepping motor section 312, a cuvette table stepping motor 313, a warming table stepping motor 314, a catcher unit stepping motor section 315, a reagent table rotary encoder section 321, a dispensing unit rotary encoder section 322, a reagent table original point sensor section 331, and a dispensing unit original point sensor section 332, and a locking mechanism 29b. The control section 300 includes a CPU 301, a ROM 302, a RAM 303, a hard disk 304, a communication interface 305, and an I/O interface 306.

The CPU 301 executes a computer program stored in the ROM 302 and a computer program loaded in the RAM 303. The RAM 303 is used to read the computer programs stored in the ROM 302 and the hard disk 304. In addition, when these computer programs are executed, the RAM 303 is used as a work area of the CPU 301. Various computer programs to be executed by the CPU 301 such as an operating system, an application program, and the like, and data used for executing the computer programs are installed on the hard disk 304. In addition, it is possible to exchange data with the information processing apparatus 3 by communication interface 305.

The CPU 301 controls the reagent bar-code reader 31, the specimen bar-code reader 52, the reagent table stepping motor section 311, the dispensing unit stepping motor section 312, the cuvette table stepping motor 313, the warming table stepping motor 314, the catcher unit stepping motor section 315, the reagent table rotary encoder section 321, the dispensing unit rotary encoder section 322, the reagent table original point sensor section 331, the dispensing unit original point sensor section 332, a remaining amount detection section 333 and a lock mechanism section 29b through the I/O interface 306.

The reagent table stepping motor section 311 includes a stepping motor 311a for rotating and driving the first reagent table 11, and a stepping motor 311b for rotating and driving the second reagent table 12 independently from the first reagent table 11. The dispensing unit stepping motor section 312 includes stepping motors 312a, 312b, 312c, 312d, and 312e for independently rotating and driving a supporting section 21a of the first specimen dispensing unit 21, a supporting section 22a of the second specimen dispensing unit 22, a supporting section 23a of the first reagent dispensing unit 23, a supporting section 24a of the second reagent dispensing unit 24, and a supporting section 25a of the third reagent dispensing unit 25, respectively. The catcher unit stepping motor section 315 includes a stepping motor 315a for rotating and driving a supporting section 26a of the first catcher unit 26, and a stepping motor 315b for rotating the second catcher unit 27.

The reagent table rotary encoder section 321 includes a rotary encoder 321a arranged in the stepping motor 311a of the first reagent table 11, and a rotary encoder 321b arranged in the stepping motor 311b of the second reagent table 12. The dispensing unit rotary encoder section 322 includes rotary encoders 322a, 322b, 322c, 322d, and 322e arranged in the respective stepping motors 312a, 312b, 312c, 312d, and 312e of the first specimen dispensing unit 21, the second specimen dispensing unit 22, the first reagent dispensing unit 23, the second reagent dispensing unit 24, and the third reagent dispensing unit 25. In addition, an incremental rotary encoder is used here. This rotary encoder is configured to output a pulse signal in accordance with a rotation displacement amount of the stepping motors, and can detect the rotation amount of the stepping motors by counting the pulse number output from the rotary encoder.

The reagent table original point sensor section 331 includes original point sensors 331a and 331b for detecting that the respective rotation positions of the stepping motor 311a of the first reagent table 11 and the stepping motor 311b of the second reagent table 12 is in the original point position. The dispensing unit original point sensor section 332 includes original point sensors 332a, 332b, 332c, 332d, and 332e for detecting that the respective rotation positions of the stepping motors 312a, 312b, 312c, 312d, and 312e of the first specimen dispensing unit 21, the second specimen dispensing unit 22, the first reagent dispensing unit 23, the second reagent dispensing unit 24, and the third reagent dispensing unit 25 is in the original point position.

The remaining amount detection section 333 includes a liquid level sensing sensor to detect remaining amounts of reagents in the reagent containers disposed in the first reagent table 11 and the second reagent table 12.

The lock mechanism section 29b is provided in the main body cover 29. The lock mechanism section 29b locks or releases the main body cover 29 when the main body cover 29 covers the mechanisms in the measurement unit 10.

Figure 6:
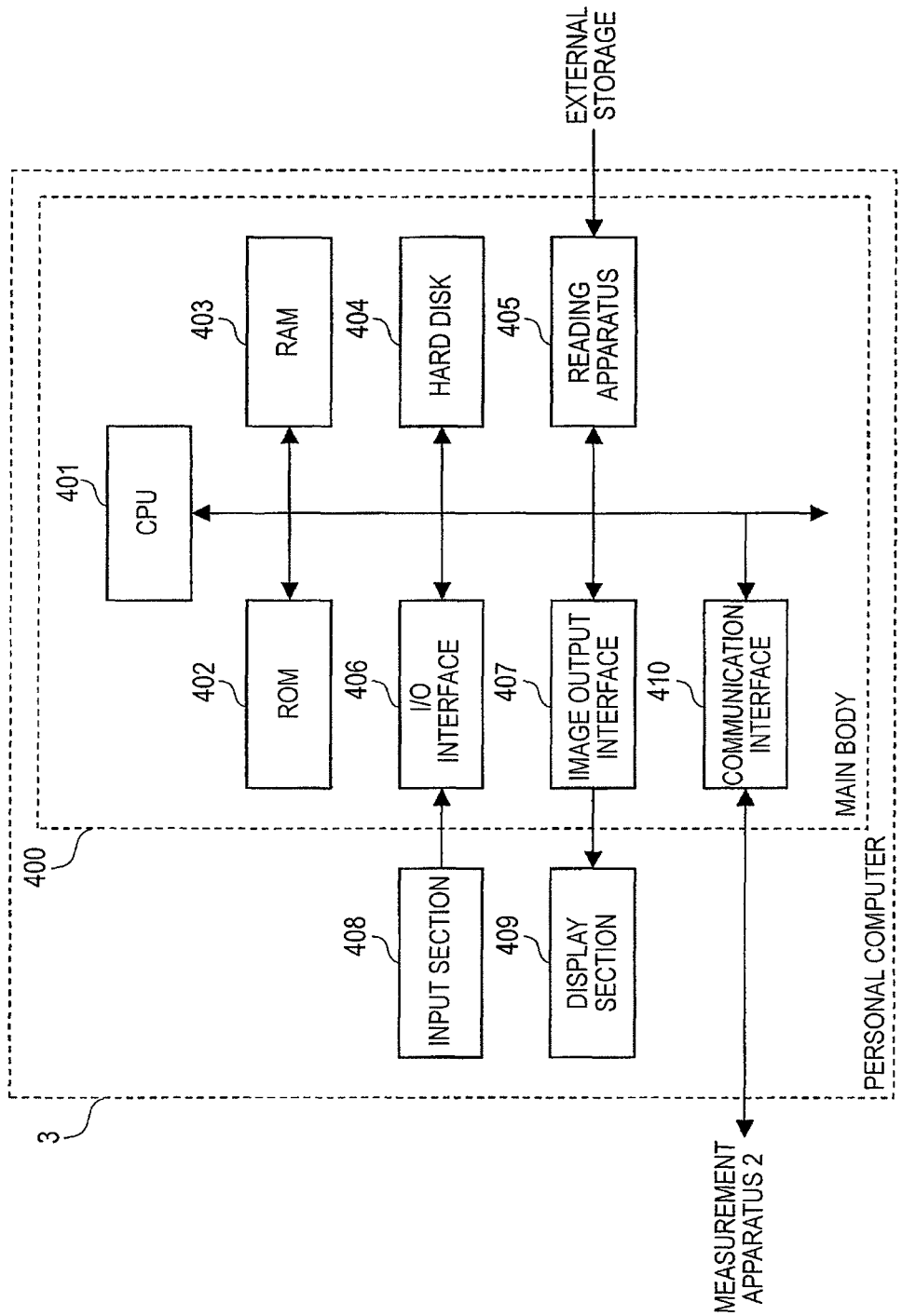
FIG. 6 is a diagram showing a circuit configuration of an information processing apparatus according to an embodiment.

FIG. 6 is a diagram showing a circuit configuration of the information processing apparatus 3.

The information processing apparatus 3 is constituted by a personal computer, and includes a main body 400, an input section 408, and a display section 409. The main body 400 includes a CPU 401, a ROM 402, a RAM 403, a hard disk 404, a reading apparatus 405, an input/output interface 406, an image output interface 407, and a communication interface 410.

The CPU 401 executes a computer program stored in the ROM 402, and a computer program loaded in the RAM 403. The RAM 403 is used to read the computer programs stored in the ROM 402 and the hard disk 404. In addition, the RAM 403 is also used as a work area of the CPU 401 when these computer programs are executed.

Various computer programs to be executed by the CPU 401 such as an operating system, an application program, and the like, and data used for executing the computer programs are installed on the hard disk 404. That is, a display program for receiving a reagent state from the measurement apparatus 2 and displaying a remaining amount of the reagent on the display section 409 as a message or the like, and an operating program for operating the measurement apparatus 2 while following the operation command for the replacement or the addition of the reagent are installed in the hard disk 404.

The reading apparatus 405 includes a CD drive, a DVD drive, or the like, and can read the computer programs and data recorded in a recording medium. The input section 408, which is constituted by a mouse and a keyboard, is connected to the input/output interface 406, and data is input to the information processing apparatus 3 when the user uses the input section 408. The image output interface 407 is connected to the display section 409, which is constituted by a display, and the like, and outputs a video signal in accordance with the image data to the display section 409. The display section 409 displays an image based on the input video signal. In addition, it is possible to exchange data with the measurement apparatus 2 by the communication interface 410.

Figure 7:
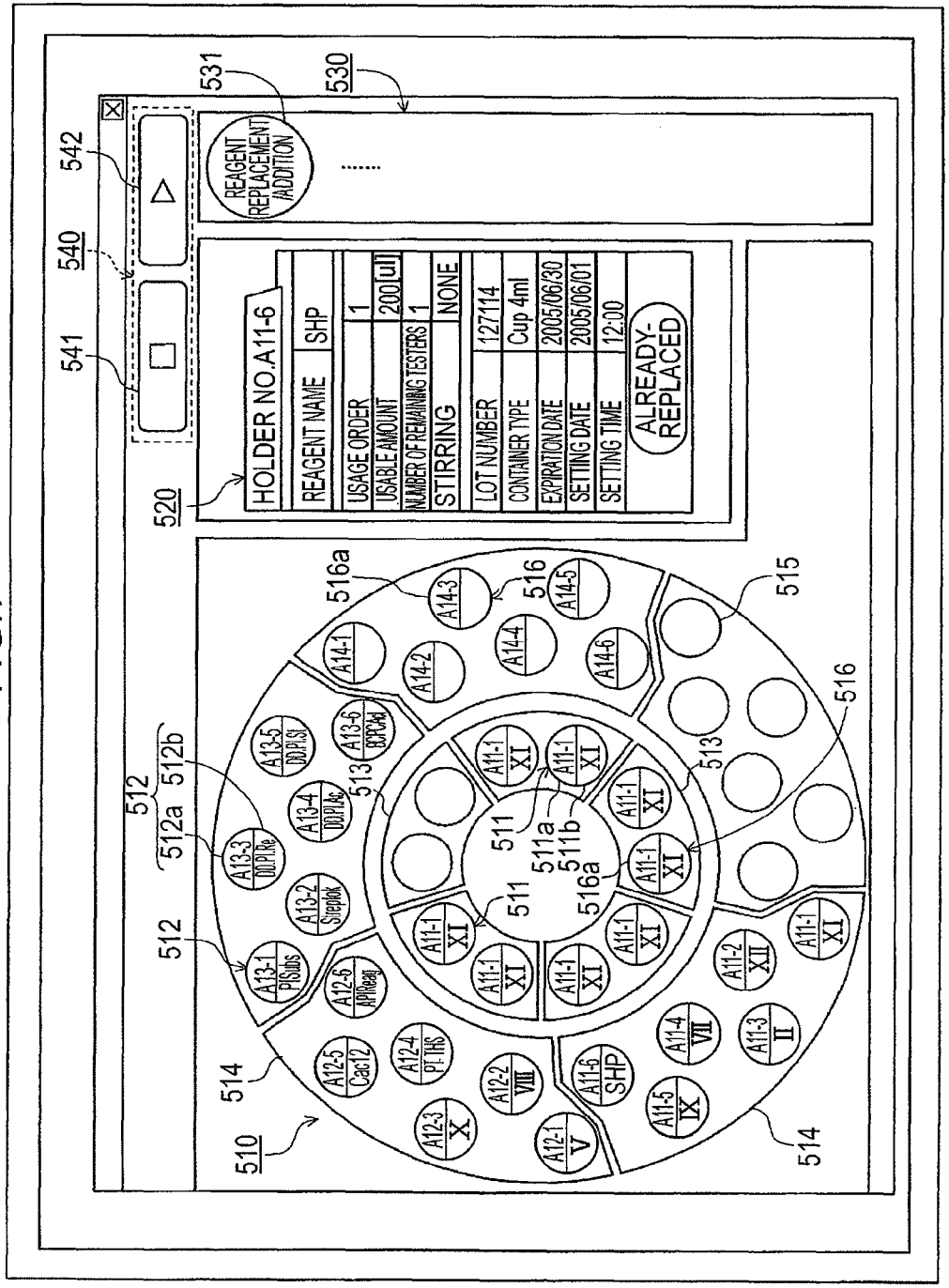
FIG. 7 is a diagram showing an example of a screen displayed on a display section of an information processing apparatus according to an embodiment.

FIG. 7 is a diagram showing an example of a screen displayed on the display section 409 of the information processing apparatus 3. The screen displayed on the display section 409 of the information processing apparatus 3 includes an arrangement display area 510, a detailed information display area 520, an operation command display area 530, and an operation determination display area 540.

The arrangement display area 510 is for displaying the positions of the first container racks 13 and the second container racks 14 arranged in the first reagent table 11 and the second reagent table 12, and the arrangement state of the reagent containers 200.

A maximum of 10 first reagent marks 511, which are displayed correspondingly to the arrangement state of the reagents with respect to the first reagent table 11, and a maximum of 30 second reagent marks 512, which are displayed correspondingly to the arrangement state of the reagents with respect to the second reagent table 12, are displayed in the arrangement display area 510. The first reagent marks 511 include a position display section 511a for displaying a position, and a name displaying section 511b for displaying the name of the reagent. In the same manner, the second reagent marks 512 include a position display section 512a for displaying a position, and a name displaying section 512b for displaying the name of the reagent.

The position information of the reagent, which is displayed on the position display section 511a of the first reagent mark 511 and the position display section 512a of the second reagent mark 512, is displayed by reading the bar-code labels attached to the first container rack 13 and the second container rack 14 using the reagent bar-code reader 31. The name of the reagent, which is displayed on the name display sections 511*b* and 512*b*, is displayed by reading the bar-code label 200*a* attached to the reagent container 200 containing the reagent, using the reagent bar-code reader 31. That is, the name of the reagent is displayed on the name display sections 511*b* and 512*b* by referring to a reagent master or the like stored in the hard disk 404 based on the bar-code information included in the bar-code label 200*a*.

The first reagent mark 511 is split and displayed by first rack marks 513 corresponding to the five first container racks 13 arranged in the first reagent table 11. The second reagent mark 512 is split and displayed by second rack marks 514 corresponding to the five second container racks 14 arranged in the second reagent table 12. With this configuration, it is possible to visually confirm on which reagent table a predetermined reagent is arranged, in which container rack the predetermined reagent is arranged, and at which position the predetermined reagent is arranged.

When a container rack is not arranged in the first reagent table 11 and the second reagent table 12, a circular rack non-arrangement mark 515, inside which nothing is displayed, is displayed. Moreover, when container racks are arranged in the first reagent table 11 and the second reagent table 12, a reagent non-arrangement mark 516 is displayed for an area corresponding to a position where reagent container 200 containing the reagent is not arranged. The reagent non-arrangement mark 516 includes a position display section 516*a* displaying position information.

When the first reagent mark 511 or the second reagent mark 512 is selected, the detailed information display area 520 displays the detailed information regarding the content of the reagent container 200 held at the selected selection mark position.

The operation command display area 530 includes a plurality of command-type buttons 531. When a user presses the command-type button 531, an operation corresponding to the above command-type button 531 is executed.

The measurement command display area 540 includes a measurement stop button 541 and a measurement start button 542. When a user presses the measurement stop button 541, a measurement suspension processing is performed. At the time of suspending the measurement, when the user presses the measurement start button 542, a measurement restart process is performed. The measurement start button 542 is effectively displayed when the measurement is executable, and a message is displayed on the screen so as to inform the user that the measurement is non-executable when the measurement start button 542 is pressed in the case in which the measurement is non-executable.

Figure 8:
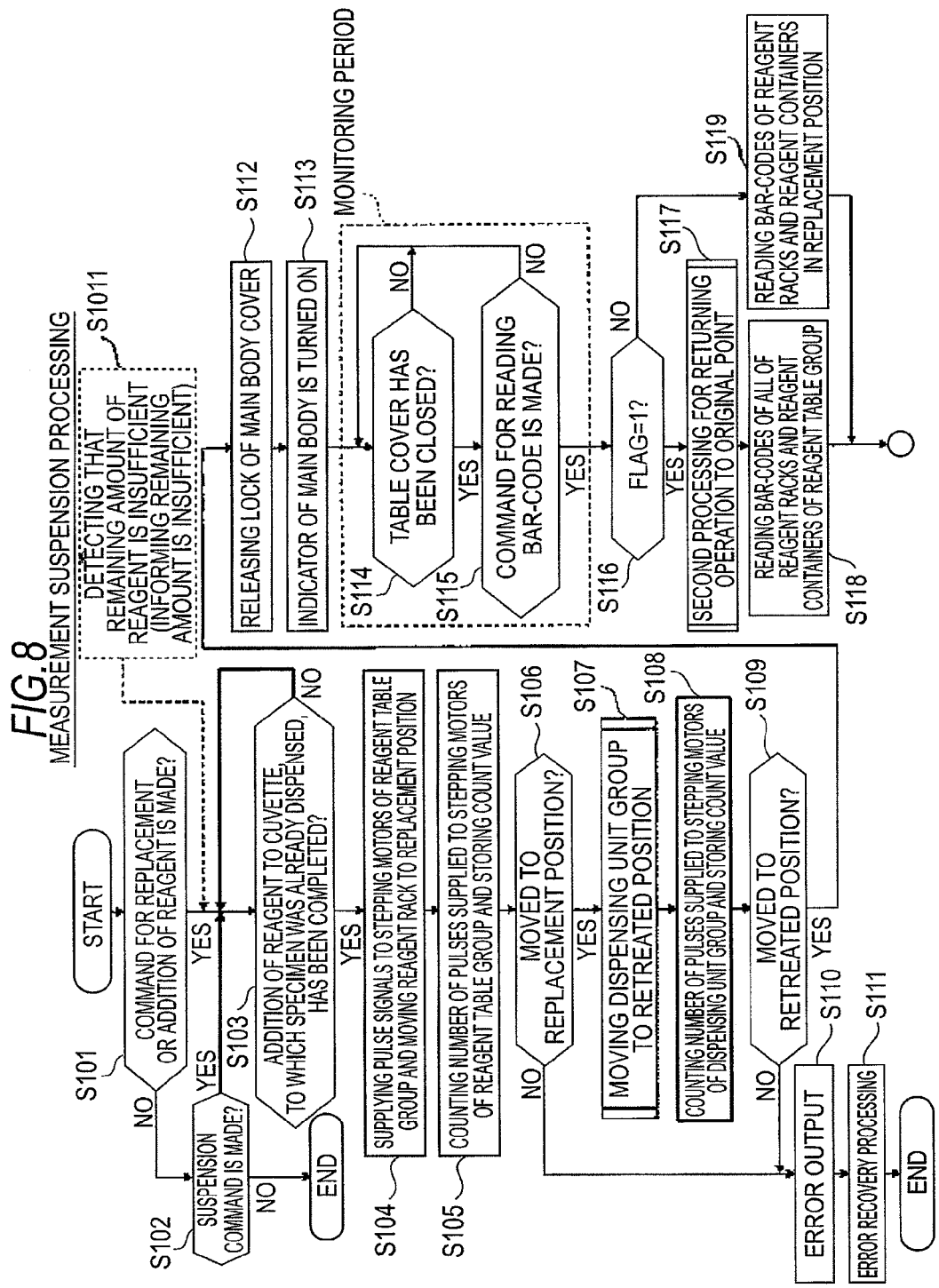
FIG. 8 is a flow chart showing a measurement suspension processing according to an embodiment.
Figure 9B:
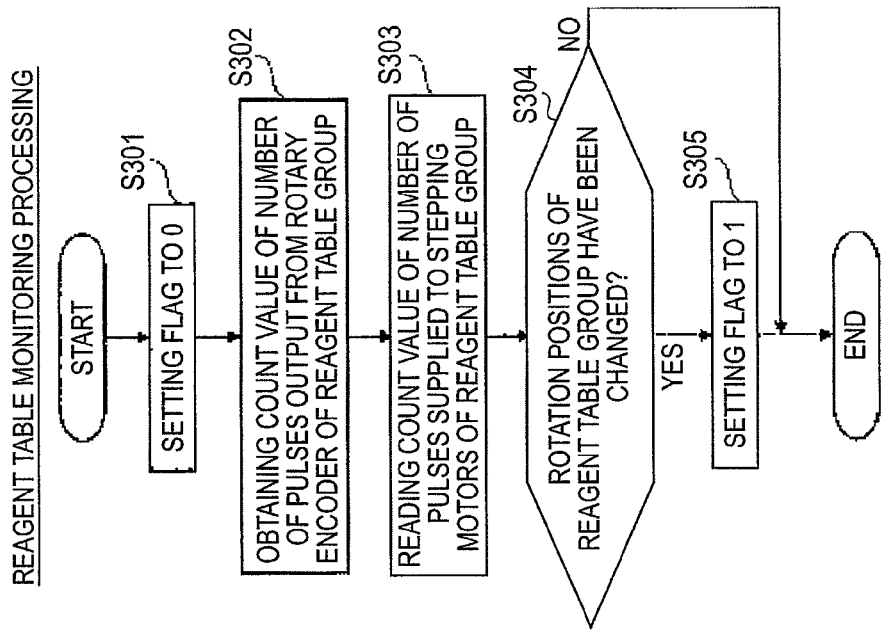
FIG. 9B is a flow chart showing a measurement suspension processing according to an embodiment.
Figure 9A:
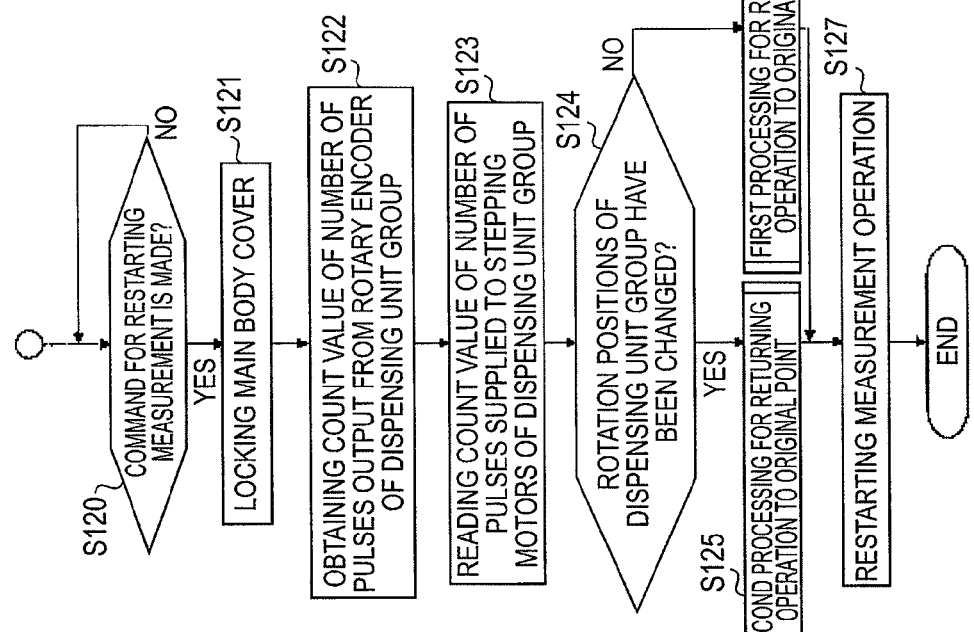
FIG. 9A is a flow chart showing a measurement suspension processing according to an embodiment.

FIGS. 8, 9A, and 9B are diagrams showing the processing flows for the measurement suspension processing according to the present embodiment. The measurement suspension processing is executed when a user commands the replacement or the addition of the reagent through the information processing apparatus 3, when the measurement stop button 541 is pressed during the measurement operation, or when the CPU 301 of the measurement apparatus 2 recognizes that the remaining amount of the reagent is insufficient. That is, although the suspension of the measurement operation is determined depending on whether or not the user inputs the command for the replacement or the addition of the reagent in S101 of FIG. 8, and is determined depending on whether or not a measurement suspension command is input in S102, the measurement suspension processing after S103 is also executed when the CPU 301 of the measurement apparatus 2 determines that the remaining amount of the reagent is insufficient (S1011). Such a measurement suspension processing is performed under the control of the control section 300. The insufficient remaining amount of the reagent is detected by the remaining amount detection section 333 shown in FIG. 5. The remaining amount detection section 333 detects remaining amounts of reagents in the reagent containers disposed in the first reagent table 11 and the second reagent table 12 by using the liquid level sensing sensor and outputs the detection result to the CPU 301. In this manner, the CPU 301 of the measurement apparatus 2 recognizes the remaining amount of the reagent in each reagent container. When the CPU 301 of the measurement apparatus 2 determines that the remaining amount of the reagent is insufficient, it is preferable to inform the user to promote the replacement of the reagent. For example, a comment "The remaining amount of reagent is insufficient. Please replace the reagent." may be displayed on the display section 409 of the information processing apparatus 3. With this operation, the reagent container can be rapidly replaced and the measurement can be restarted.

During the measurement operation, when the replacement or the addition of the reagent is commanded by pressing the command-type button 531 for "the replacement/addition of the reagent" in the operation command display area 530 shown in FIG. 7 (S101: YES), the processing proceeds to S103. When such a command is not made (S101: NO), the processing proceeds to S102. In addition, during the measurement operation, when the measurement stop button 541 in the measurement command display area 530 shown in FIG. 7 is pressed (S102: YES), the processing proceeds to S103. When such a command is not made (S102: NO), the processing flow ends. When a command for the replacement or the addition of the reagent in S101 or a suspension command in S102 is made, a suctioning for new specimens performed by the first specimen dispensing unit 21 and the second specimen dispensing unit 22 is suspended.

If the reagent addition to the cuvette, to which the specimen was already dispensed, is completed after the suspension of the suctioning of the new specimens performed by the first specimen dispensing unit 21 and the second specimen dispensing unit 22 (S103: YES), the processing proceeds to S104. If the reagent addition to the cuvette, to which the specimen was already dispensed, is not completed (S103: NO), the processing flow is put on standby until such a reagent addition is completed. In greater detail, when the necessary reagent is added to the cuvette, to which the specimen was already dispensed, and then the cuvette is set in the holding hole 41 of the detection unit 40, the processing proceeds to S104. When the cuvette is set in the holding hole 41 of the detection unit 40, optical information is detected from the sample for measurement in the cuvette set in the holding hole 41 even during the processing after S104. Accordingly, even when the measurement process is suspended in midflow, it is possible to prevent the alteration of the specimen, which occurs by leaving the dispensed specimen.

In addition, when the reagent addition to the cuvette, to which the specimen was already dispensed, is completed, it is not necessary to drive the reagent table group and the dispensing unit group. In this case, as described above, the dispensing unit group is driven and put on standby such that the pipettes thereof are contained in the pipette cleaners 38*a* to 38*e*. Also in this case, as described above, the first reagent dispensing unit 23 is lifted in a timely manner from the pipette cleaner 38*c* and rotated and driven when the disposal of the cuvette is performed by the second catcher unit 27.

In S104, the stepping motors 311*a* and 311*b* (see FIG. 5) of the reagent table group are supplied with pulse signals, respectively, and the reagent table group is rotated and driven such that the reagent container for which the replacement or the addition of the reagent is commanded is positioned within the replacement area shown in FIG. 4B. When the replacement or the addition of the reagent is commanded without the designation of the reagent container to be replaced or added, the pulse signal is not supplied to the stepping motors of the reagent table group. When the measurement apparatus 2 recognizes that the reagent in the reagent container is running out, the reagent table group is rotated and driven such that such a reagent container is positioned within the replacement area.

In S105, the pulse is supplied to the stepping motors of the reagent table group by the time that the reagent table group is rotated and driven so as to be positioned in the replacement area in S104. The count value of the pulse number corresponding to the rotation position from the original point position is updated based on the pulse number supplied at this time. Such a count value is updated and stored in the RAM 303 of the measurement apparatus 2 as needed. With such a configuration, it is possible to identify the rotation positions of the reagent table group after they are moved to the replacement positions, based on the count value stored in the RAM 303.

When the reagent table group is rotated and driven and the reagent container, which is designated for the replacement or the addition of the reagent, is not moved to the replacement area (S106: NO), the processing proceeds to S110. The moving of the reagent container to the replacement area is determined by, for example, determining whether or not the above-described count value of the pulse number from the original point position corresponds to a value corresponding to the replacement area. When such a reagent container is moved to the replacement area (S106: YES), the processing proceeds to S107. In S107, the dispensing unit group is moved to the retreated position shown in FIG. 4B.

Here, by referring to FIG. 10, a processing content of "moving dispensing unit group to retreated position" shown in S107 of FIG. 8 will be described.

In S201, the second reagent dispensing unit 24 and the third reagent dispensing unit 25 are moved upward (Z-axis positive direction) by a predetermined distance. The pipettes of the second reagent dispensing unit 24 and the third reagent dispensing unit 25 are contained in the pipette cleaners 38*d* and 38*e* as described above in S103 of FIG. 8. That is, in this embodiment, these dispensing units are positioned in the retreated position. In this state, these dispensing units are moved upward (Z-axis positive direction) by a predetermined distance. So, when the reagent is replaced or added, the situation hardly arises in which a user touches these dispensing units and the pipettes are thus moved and come into contact with the mechanisms disposed in the base of the measurement apparatus 2. Accordingly, it is possible to prevent the pipettes of the dispensing units from being broken.

In S202, the first specimen dispensing unit 21 and the second specimen dispensing unit 22 are moved upward (Z-axis positive direction) by a predetermined distance. So, the pipettes of the dispensing units are positioned just above the pipette cleaners 38*a* and 38*b*, respectively. Accordingly, in the subsequent steps, these dispensing units enter a state so as to be rotated and driven.

In S203, the stepping motor 312*a* (see FIG. 5) of the first specimen dispensing unit 21 is supplied with pulse signals and thus the first specimen dispensing unit 21 is rotated and driven so as to be positioned at the retreated position.

In S204, it is determined whether the first reagent dispensing unit 23 is positioned at the retreated position. When the first reagent dispensing unit 23 is positioned at the retreated position (S204: YES), the processing proceeds to S205. When the first reagent dispensing unit 23 is not positioned at the retreated position (S204: NO), the processing proceeds to S207.

The pipette of the first reagent dispensing unit 23 is contained in the pipette cleaner 38*c* and enters a standby state in principle when the reagent addition to the cuvette, to which the specimen was already dispensed, is completed, in S103 of FIG. 8. In this case, in S204, it is determined that the first reagent dispensing unit 23 is positioned at the retreated position. However, as described above, during the standby state, when the disposal of the cuvette is performed by the second catcher unit 27, the first reagent dispensing unit 23 is evaded from the cuvette disposal route so as not to disturb the cuvette disposal of the second catcher unit 27. In this case, in S204, it is determined that the first reagent dispensing unit 23 is not positioned at the retreated position.

When it is determined the first reagent dispensing unit 23 is positioned at the retreated position in S204, the first reagent dispensing unit 23 is moved upward (Z-axis direction) by a predetermined distance in S205. In this manner, as in the second reagent dispensing unit 24 and the third reagent dispensing unit 25, the pipette of the first reagent dispensing unit 23 can be prevented from being broken through contact at the time of replacing or adding the reagent.

In S206, the stepping motor 312*b* (see FIG. 5) of the second specimen dispensing unit 22 is supplied with pulse signals and thus the second specimen dispensing unit 22 is rotated and driven so as to be positioned at the retreated position. Accordingly, "moving dispensing unit group to retreated position" is completed.

On the other hand, it is determined that the first reagent dispensing unit 23 is not positioned at the retreated position in S204, the stepping motor 312*c* (see FIG. 5) of the first reagent dispensing unit 23 is supplied with pulse signals in S207 and thus the first reagent dispensing unit 23 is rotated and driven so as to be positioned at the retreated position. After that, the processing returns to S204.

As described above, when the first reagent dispensing unit 23 is retreated and then the second specimen dispensing unit 22 is allowed to be moved to the retreated position, the contact between the second specimen dispensing unit 22 and the first reagent dispensing unit 23 can be prevented. That is, as described above, since the first reagent dispensing unit 23 is rotated and driven so as not to disturb the cuvette disposal of the second catcher unit 27, there is a concern that the second specimen dispensing unit 22 and the first reagent dispensing unit 23, of which the rotation driving routes overlap with each other, come into contact with each other when the moving of the dispensing unit group to the retreated position is started at the same time. However, when the second specimen dispensing unit 22 is positioned at the retreated position as described above, the first reagent dispensing unit 23 is positioned at the retreated position and then the second specimen dispensing unit 22 is moved to the retreated position, and thus the contact between these dispensing units can be avoided.

Returning to FIG. 8, in S108, the number of the pulses, which was supplied to the stepping motors 312*a* to 312*e* (see FIG. 5) of the dispensing unit group when the dispensing unit group was moved to the retreated position in S107, is counted, and the count value of the pulse number corresponding to the rotation position from the original point position is updated. This count value is updated and stored in the RAM 303 of the measurement apparatus 2 as needed. With this configuration, it is possible to identify the rotation positions of the dispensing unit group after they are moved to the retreated positions based on the count value stored in the RAM 303.

If the dispensing unit group has been moved to the retreated position (S109: YES), the processing proceeds to S112. When the dispensing unit group has not been moved to the retreated position (S109: NO), the processing proceeds to S110. Here, whether the dispensing unit group has been moved to the retreated position is determined depending, for example, on whether the count value of the pulse number from the above-described original point position has become the value corresponding to the replacement position.

In S110, an error message is output to the display section 409 of the information processing apparatus 3 so as to inform that the movement of the reagent table group to the replacement area or the movement of the dispensing unit group to the retreated position is in an error state. In S111, an error recovery processing is executed so as to be able to start the restarting of the processing flow of the measurement suspension processing, and the processing flow is terminated.

If the reagent table group has been moved to the replacement area, and the dispensing unit group has been moved to the retreated position in this manner, the lock of the main body cover 29 is released in S112, and the indicator of the main body is turned on in S113. With such a configuration, a user can know that replacement or the addition of the reagent can be performed by opening the main body cover of the measurement apparatus 2. Thereafter, the user opens the main body cover 29 of the measurement apparatus 2, opens the table cover 17, and performs the replacement or the addition of the reagent.

If the replacement or the addition of the reagent by the user has been completed, and the table cover 17 has been closed (S114: YES), the processing proceeds to S115. If the table cover 17 has not been closed (S114: NO), the processing flow is put on standby until the table cover 17 is closed.

Thereafter, if the table cover 17 is closed (S114: YES), it is determined that the user has input the command for reading the bar-code label through the information processing apparatus 3 (S115). If the command for reading the bar-code label has been input (S115: YES), the processing proceeds to S116, and if the command for reading the bar-code label has not been input (S115: NO), the processing flow is put on standby until the command for reading the bar-code label is input.

Here, the following processing is performed in a parallel manner during the period from when the indicator of the main body is turned on (S113) to S116 (hereinafter, referred to as a "monitoring period"). This processing is repeatedly performed at an interval of once every 100 ms.

FIG. 9B is a diagram showing a processing flow of a processing performed during the monitoring period.

In S301, a flag value stored in the RAM 303 of the measurement apparatus 2 is set to 0. In S302, the count value of the pulse number output from the rotary encoder section 321 of the reagent table group is obtained. In S303, the count value stored in S104, that is, the count value of the pulse number supplied to the stepping motors 311a and 311b of the reagent table group is read.

The rotation position on the basis of the count value of the pulse number output from the rotary encoder section 321 of the reagent table group, which was obtained in S302, and the rotation position on the basis of the count value of the pulse number supplied to the stepping motors 311a and 311b of the reagent table group, which was stored in S104, are compared, and it is determined whether the rotation positions of the reagent table group have been changed from the replacement areas (S304). Here, if the rotation position of at least one reagent table has been changed from the replacement area (S304: YES), the processing proceeds to S305. That is, when it was determined that the reagent table group was moved from the time point when it became possible to perform the replacement or the addition of the reagent, the processing proceeds to S305. In S305, the flag is set to 1, and the processing flow is terminated. In addition, when any of the rotation positions of the reagent tables have not been changed from the replacement area (S304: NO), the processing flow is terminated without changing the flag to 1.

Such a processing is repeatedly performed at short intervals of once every 100 ms during the monitoring period. If the position of the reagent table group is moved by the contact of the user's finger or the like at each period of performing processing, the flag value is set to 1 for the processing in the corresponding time. If the position of the reagent table group is not moved at all during the monitoring period, the flag value is still 0.

Referring again to FIG. 8, if the determination has been made to be YES in S115, then it is determined whether the flag value is 1 in S116. If the flag value is 1 (S116: YES), the processing proceeds to S117, and if the flag value is not 1 (S116: NO), the processing proceeds to S119.

In S117, a second processing for a returning operation to an original point is performed to match the original point positions of the reagent table group. With this processing, the rotation positions of the reagent table group are appropriately adjusted. The description will be made later regarding the second processing for the returning operation to the original point, with reference to FIGS. 11C and 11D. Such a returning operation to the original point may be performed only for the reagent table whose rotation position has been changed from the replacement area, or may be uniformly performed for all the reagent tables.

In S118, all the bar-code labels of all the reagent containers 200 and the reagent racks arranged in the reagent table group are read. In S119, the bar-code labels of all the reagent containers 200 and the reagent racks in the replacement area are read.

FIG. 9A is a diagram showing the processing flow following S118 and S119 shown in FIG. 8.

If the user inputs the command to restart the measurement by pressing the measurement start button 542 (see FIG. 7) in the measurement command display area 540 (S120: YES), the processing proceeds to S121. If the command to restart the measurement is not made (S120: NO), the processing flow is put on standby until the command is made.

In S121, the main body cover is locked. In S122, the count value of the pulse number output from the rotary encoder section 322 of the dispensing unit group is obtained. In S123, the count value stored in S108, that is, the count value of the pulse number supplied to the stepping motors 312a to 312e of the dispensing unit group is read.

The rotation position on the basis of the count value of the pulse number output from the rotary encoder section 322 of the dispensing unit group, which was obtained in S122, and the rotation position on the basis of the count value of the pulse number supplied to the stepping motors 312a to 312e of the dispensing unit group, which was stored in S108, are compared to determine whether the rotation positions of the dispensing unit group have been changed from the retreated position (S124). Here, if the rotation position of at least one dispensing unit has been changed from the retreated position (S124: YES), the processing proceeds to S125. That is, when it is determined that the dispensing unit group was moved when it became possible to perform the replacement or the addition of the reagent, the processing proceeds to S125. When any rotation positions of the dispensing units have not been moved from the retreated position (S124: NO), the processing proceeds to S126.

In S125, the second processing for the returning operation to the original point is performed to match the original point positions of the dispensing unit group. With this operation, the rotation positions of the dispensing unit group are appropriately adjusted. In S126, the first processing for the returning operation to the original point is performed to match the original point positions of the dispensing unit group. With this operation, the rotation positions of the dispensing unit group are appropriately adjusted. In the first processing for the returning operation to the original point, the matching of the original point positions is simply performed as compared with the second processing for the returning operation to the original point.

That is, in the case in which a user touched the dispensing unit group, and the rotation positions of the dispensing unit group have been changed during the replacement or the addition of the reagent, the second processing for the returning operation to the original point with higher precision is performed. On the other hand, when the rotation positions of the dispensing unit group have not been changed, the rotation positions of the dispensing unit group are in the same state as that when they were appropriately recognized, and therefore, the first processing for the returning operation to the original point, by which it is possible to match the original point positions in a short time, is performed. The first processing for the returning operation to the original point will be described later with reference to FIGS. 11A and 11B.

In S127, the measurement operation is restarted, and the processing flow is terminated.

FIGS. 11A to 11D are diagrams showing the processing contents of the first processing for the returning operation to the original point and the second processing for the returning operation to the original point. FIGS. 11A and 11B are diagrams showing the processing flow of the first processing for the returning operation to the original point and specific processing contents, respectively. FIGS. 11C and 11D are diagrams showing the processing flow of the second processing for the returning operation to the original point and specific processing contents, respectively. In FIGS. 11B and 11D, the horizontal axis represents the time, and the vertical axis represents the speed.

First, a trapezoidal drive and a constant speed drive will be described with reference to FIG. 11B.

The trapezoidal drive is a drive procedure in which the rotation speed of the stepping motor is increased with the passage of time, and becomes constant when it reaches a predetermined speed, and is decreased with the passage of time when it meets a predetermined condition, as shown in FIGS. 11B and 11D. In addition, the constant speed drive is a drive procedure in which the stepping motor is driven at a predetermined speed, and stopped when the speed meets a predetermined condition, as shown in FIGS. 11B and 11D.

As shown in FIG. 11A, in the first processing for the returning operation to the original point, the stepping motor is subjected to the trapezoidal drive, and the rotation position of the stepping motor is moved to a near-original point position in S11. Here, the near-original point position is a position from which the rotation position of the stepping motor can be appropriately adjusted to the original point position when the stepping motor is subjected to the constant speed drive from the near-original point position next time. The speed of the stepping motor is decreased at a predetermined rotation position before the near-original point position. In this manner, the rotation position of the stepping motor is positioned at the near-original point position when the trapezoidal drive is completed.

If the rotation position of the stepping motor has been matched to the near original point position, the stepping motor is then subjected to the constant speed drive in S12, and the rotation position of the stepping motor is eventually matched to the original point position. The first processing for the returning operation to the original point is performed in the case in which the rotation positions of the dispensing unit group have not been changed, as shown in S126 of FIG. 9A. That is, since the position information of the stepping motor is in the same state as that when it is appropriately recognized in the case in which the rotation positions of the dispensing unit group have not been changed, the first processing for the returning operation to the original point, which can perform the original point position matching in a shorter time, is employed.

As shown in FIGS. 11C and 11D, in the second processing for the returning operation to the original point, the stepping motor is subjected to the trapezoidal drive in S21, the speed of the stepping motor is decreased when it is detected that the rotation position of the stepping motor has passed the original point position (original point detection), and the rotation direction of the stepping motor is then reversed.

In S22, the stepping motor is subjected to the trapezoidal drive in the reverse direction with respect to the rotation direction in S21, the speed of the stepping motor is decreased if the original point has been detected again, and the rotation direction of the stepping motor is then reversed to shift to the constant drive.

In S23, the stepping motor is subjected to the constant speed drive in the reverse direction with respect to the rotation direction in S22, and the rotation direction of the stepping motor is reversed when the original point is detected again. At this time, the position at which the speed of the stepping motor becomes 0 becomes a first near-original point position. Here, the first near-original point position is a position from which the rotation position of the stepping motor can be matched to the second near-original point position, which is substantially the same position as the near-original point position shown in FIG. 11B, if the stepping motor is subjected to the trapezoidal drive from the first near-original point position next time.

In S24, the stepping motor is subjected to the trapezoidal drive, and the rotation direction of the stepping motor is reversed when the original point is detected. At this time, the position at which the speed of the stepping motor becomes 0 becomes the second near-original point position. In S25, the stepping motor is subjected to the constant speed drive, and the rotation position of the stepping motor is eventually matched to the original point position.

As described above, in the second processing for the returning operation to the original point, it is possible to more precisely match the rotation position to the original point position by performing more steps than that in the first processing for the returning operation to the original point. Accordingly, this is performed in the case in which the encoder values of the reagent table group and the dispensing unit group have been changed, as shown in S117 of FIG. 8 and S125 of FIG. 9A.

According to this embodiment, when the measurement operation is suspended, the dispensing unit group is positioned at the retreated position and thus a space where the reagent can be replaced or added is formed from above the reagent table group (Z-axis positive direction) to the front of the measurement apparatus 2. Accordingly, a user can perform the replacement or the addition of the reagent via the replacement area shown in FIG. 4B without touching the dispensing unit group during the suspension of the measurement operation.

In addition, according to this embodiment, when the measurement operation is suspended, the dispensing unit group is retreated outside the area of the table cover 17 shown in FIG. 4A such that a user can easily replace or add the reagent. Accordingly, when the measurement is performed, each dispensing unit may be moved so as to reach the space from above the reagent table group (Z-axis positive direction) to the front of the measurement apparatus 2 as described above, and thus the degree of freedom in the arrangement layout of the dispensing unit group which is disposed around the reagent table group can be increased.

According to this embodiment, the dispensing unit group is positioned at the retreated position and then the lock of the main body cover is released. Accordingly, the contact of a user replacing or adding the reagent with the dispensing unit can be reliably suppressed.

According to this embodiment, since the retreated positions of the first reagent dispensing unit 23, the second reagent dispensing unit 24 and the third reagent dispensing unit 25 are the same as the cleaning positions of these dispensing units, respectively, the rotation of these dispensing units can be easily controlled.

Although the embodiment of the present invention was described above, the present invention is not limited thereto. In addition, the embodiment of the present invention can be modified in various ways in addition to the above configuration.

For example, in the above-described embodiment, the retreated position of the dispensing unit group is set as shown in FIG. 4B. However, the retreated position may be disposed anywhere if it does not disturb the replacement or the addition of the reagent by a user. For example, a hole may be provided in the base of the apparatus and at least one dispensing arm may be moved downward to the hole. In this manner, the contact of the user with the dispensing unit group can be suppressed during the replacement or the addition of the reagent by the user.

In the above-described embodiment, the rotation positions of the first reagent dispensing unit 23, the second reagent dispensing unit 24 and the third reagent dispensing unit 25, each positioned at the retreated position, are respectively the same as the rotation positions when these dispensing units are positioned in the corresponding pipette cleaners. However, the rotation positions of these dispensing units, each positioned at the retreated position, may be different from the rotation positions when these dispensing units are positioned in the pipette cleaners.

In the above-described embodiment, the discharging positions of the dispensing unit group are the areas just above the pipette cleaners 38a to 38e cleaning the pipettes of the dispensing units. However, the discharging positions may be disposed at other positions.

In the above-described embodiment, during the suspension of the measurement, only the dispensing unit group is retreated to the retreated position. However, the first catcher unit 26, the second catcher unit 37 and the third catcher unit 28 also may be retreated to predetermined retreated positions, respectively.

In the above-described embodiment, when a reagent replacement command or a measurement suspension command is made, all the dispensing units are retreated to the retreated positions. However, the dispensing units, which do not pass through the area above the above-described replacement area in which the reagent container is replaced and do not disturb the replacement of the reagent container, may not be moved to the retreated positions. In addition, even when a reagent replacement command or a measurement suspension command is made, the dispensing units which do not disturb the replacement of the reagent container may continue the dispensing operation.

In the above-described embodiment, when a reagent replacement command or a measurement suspension command is received during the continuous measurement, the dispensing units are retreated to the retreated positions. However, even when a reagent replacement command is received while the continuous measurement is not being performed, the dispensing units may be retreated to the retreated positions. For example, when the measurement apparatus is in a standby state and a reagent replacement command is received, the dispensing units may be retreated to the retreated positions.

In the above-described embodiment, the necessary reagent is added to the cuvette, to which the specimen was already dispensed, the cuvette is set in the holding hole 41 of the detection unit 40, and then the dispensing unit group is moved to the retreated position. However, the present invention is not limited to this. When the necessary reagent is added to the cuvette, to which the specimen was already dispensed, the dispensing unit group may be accordingly moved to the retreated position.

In the above-described embodiment, when a measurement restart command is received, the suspended measurement operation is restarted (see S120 of FIG. 9A). However, the measurement operation may be automatically restarted when the closing of the main body cover 29 of the measurement apparatus 2 is detected.

In the above-described embodiment, the table cover 17 covering the reagent table group is configured such that only half thereof is openable. However, the table cover 17 covering the reagent table group may be configured so as to be entirely openable. For example, the table cover 17 may be configured so as to be detachable.

In the above-described embodiment, when a command for the replacement or the addition of the reagent is made by a user or the measurement apparatus 2 recognizes that the reagent is running out, the processing flows for the measurement suspension processing are executed. However, the present invention is not limited to this. For example, even when the measurement suspension processing is executed due to the detection of an error in the measurement apparatus 2, the dispensing unit group may be retreated to the retreated position shown in FIG. 4B.

In the above-described embodiment, the specimen analyzing apparatus 1 is a blood coagulation analyzing apparatus. However, the present invention is not limited to this. The specimen analyzing apparatus 1 may be an apparatus for measuring a clinical specimen by using a reagent, such as an immuno-analyzer for measuring a serum, a blood cell counting apparatus for counting the number of blood cells in the blood, a urine analyzer for measuring urine or an analyzing apparatus for analyzing bone marrow fluid.

In the above-described embodiment, the reagent is replaced or added via the replacement area. However, at least one of the removal of the reagent, setting of the reagent and adding of the reagent may be performed via the container replacement area. For example, the setting of the reagent and adding of the reagent may be performed in an area other than the container replacement area, and the removal of the reagent may be performed via the container replacement area. Alternatively, the removal of the reagent may be performed in an area other than the container replacement area, and the setting of the reagent and adding of the reagent may be performed via the container replacement area.

In addition to the above description, the embodiment of the present invention can be appropriately modified in various ways within the scope of the technical spirit shown in the range of the claims.

What is claimed is:

1. A specimen analyzing apparatus for measuring a specimen by using a reagent in a reagent container, comprising:
   a plurality of dispensing mechanisms each of which includes a dispensing tube rotatably movable to a container removal area to suction and discharge a liquid;
   a reagent container holder from which the reagent container is removable when the reagent container is placed in the container removal area;
   a reagent table on which the reagent container in the reagent container holder is placed and which is automatically movable relative to the container removal area; and
   a controller programmed to control rotation of the plurality of dispensing mechanisms, movement of the reagent table, and to receive a replacement command for a replacement of the reagent and to control the plurality of dispensing mechanisms to move each dispensing tube of the plurality of dispensing mechanisms thereby removing each dispensing tube of the plurality of dispensing mechanisms from the container removal area when the replacement command has been received by the controller.

2. The specimen analyzing apparatus according to claim 1, wherein the controller is further programmed to control the plurality of dispensing mechanisms to remove each dispensing tube of the plurality of dispensing mechanisms from the container removal area to retreated positions which do not interfere with replacing the reagent container by an operator.

3. The specimen analyzing apparatus according to claim 2, further comprising:
   a main body cover to cover at least the plurality of dispensing mechanisms and the reagent container holder,
   wherein the retreated positions are positions where the dispensing tubes of the plurality of dispensing mechanisms do not interfere with a replacement route,
   wherein the replacement route defines a route to replace the reagent container by the operator, and
   wherein the route extends from an open-side space, which is accessible when the main body cover is opened, to a space above the container removal area.

4. The specimen analyzing apparatus according to claim 3, wherein the plurality of dispensing mechanisms are configured to move the dispensing tubes to reach the replacement route and to perform suctioning and discharging during a measurement operation.

5. The specimen analyzing apparatus according to claim 3, further comprising:
   a cleaning section to clean the dispensing tubes,
   wherein the cleaning section is located outside the replacement route and is provided with opening sections, and
   wherein the retreated positions are positions in which the dispensing tubes of the plurality of dispensing mechanisms are positioned above the opening sections of the cleaning section.

6. The specimen analyzing apparatus according to claim 3, further comprising:
   a lock mechanism to lock the main body cover,
   wherein the controller is further programmed to control the lock mechanism to release the lock of the main body cover when the dispensing tubes of the plurality of dispensing mechanisms are retreated to the retreated positions.

7. The specimen analyzing apparatus according to claim 2, wherein the plurality of dispensing mechanisms is configured such that the dispensing tubes of the plurality of dispensing mechanisms can be moved to original point positions, to suctioning positions, to discharging positions and to the retreated positions, and
   wherein the retreated positions are different from the original point positions.

8. The specimen analyzing apparatus according to claim 2, further comprising:
   an informing section to inform that the reagent can be replaced when each dispensing tube is removed to the retreated positions.

9. The specimen analyzing apparatus according to claim 1, further comprising:
   a memory to store control data;
   a reaction container holder to hold a reaction container containing a specimen dispensed from a specimen container,
   wherein the controller is further programmed to control the plurality of dispensing mechanisms based on the control data such that when the receiving section receives the replacement command while the reaction container holder holds the reaction container containing the specimen the reagent in the reagent container held in the reagent container holder is dispensed to the reaction container, to which the specimen was already dispensed, and then the dispensing tube is retreated from the container removal area.

10. The specimen analyzing apparatus according to claim 9, further comprising:
    a detection section to detect component information relating to components included in a measurement sample, which is prepared from the specimen and the reagent; and
    a transport section to transport the reaction container to the detection section,
    wherein the controller is further programmed to control the plurality of dispensing mechanisms to remove the dispensing tubes of the plurality of dispensing mechanisms to the retreated positions after the reaction container is transported to the detection section by the transport section, and
    wherein the detection section detects the component information relating to the components included in the measurement sample in the reaction container when the reaction container is transported from the transport section.

11. The specimen analyzing apparatus according to claim 1,
    further comprising another dispensing mechanism different from the plurality of dispensing mechanisms,
    wherein the controller is further programmed to control the plurality of dispensing mechanisms to remove each dispensing tube of the plurality of dispensing mechanisms and a dispensing tube of the another dispensing mechanism from the container removal area when the receiving section receives the replacement command.

12. The specimen analyzing apparatus according to claim 1,
    wherein each dispensing tube is configured to perform one of:
    suctioning and discharging the specimen; and
    suctioning and discharging the reagent.

13. The specimen analyzing apparatus according to claim 1, further comprising a stepping motor to move one of the plurality of dispensing mechanisms,
   wherein the controller is further programmed to control the stepping motor to move a dispensing tube of the plurality of dispensing mechanisms without moving the reagent container holder.

14. A specimen analyzing apparatus for measuring a specimen by using a reagent, comprising:
   a plurality of dispensing mechanisms each of which includes a dispensing tube rotatably movable to a container removal area to suction and discharge a liquid;
   a reagent container holder from which a reagent container is removable when the reagent container is being placed in the container removal area;
   a remaining amount detection section to detect a remaining amount of the reagent in the reagent container held in the reagent container holder;
   a reagent table on which the reagent container in the reagent container holder is placed and which is automatically movable relative to the container removal area; and
   a controller programmed to control movement of the reagent table and control the plurality of dispensing mechanisms to move each dispensing tube of the plurality of dispensing mechanisms thereby removing each dispensing tube of the plurality of dispensing mechanisms from the container removal area when it is determined by the remaining amount detection section on the basis of a detection result that the remaining amount of the reagent in the reagent container held in the reagent container holder is insufficient.

15. The specimen analyzing apparatus according to claim 14,
   wherein the controller is further programmed to control the plurality of dispensing mechanisms to remove each dispensing tube of the plurality of dispensing mechanisms to retreated positions which do not interfere with replacing the reagent container by an operator from the container removal area.

16. The specimen analyzing apparatus according to claim 15, further comprising:
   a main body cover to cover at least the plurality of dispensing mechanisms and the reagent container holder,
   wherein the retreated positions are positions where the dispensing tubes of the plurality of dispensing mechanisms do not interfere with a replacement route to replace the reagent container,
   wherein the replacement route defines a route to replace the reagent container by the operator, and
   wherein the route extends from an open-side space which is accessible when the main body cover is opened, to a space above the container removal area.

17. The specimen analyzing apparatus according to claim 16,
   wherein the plurality of dispensing mechanisms are configured to move each dispensing tube of the plurality of dispensing mechanisms to reach a position on the replacement route and to perform suctioning and discharging during the measurement operation.

18. The specimen analyzing apparatus according to claim 16, further comprising:
   a cleaning section to clean the dispensing tubes of the plurality of dispensing mechanisms,
   wherein the cleaning section is located outside the replacement route and is provided with opening sections, and
   wherein the retreated positions are positions in which the dispensing tubes of the plurality of dispensing mechanisms are positioned above the opening sections of the cleaning section.

19. The specimen analyzing apparatus according to claim 15,
   wherein the plurality of dispensing mechanisms are configured such that each dispensing tube of the plurality of dispensing mechanisms can be moved to original point positions, to suctioning positions, to discharging positions and to the retreated positions, and
   wherein the retreated positions are different from the original point positions.

20. The specimen analyzing apparatus according to claim 14, further comprising:
   an informing section for performing an informing operation on the basis of the detection result of the remaining amount detection section to replace the reagent when it is determined by the remaining amount detection section that the remaining amount of the reagent in the reagent container held in the reagent container holder is insufficient.

21. The specimen analyzing apparatus according to claim 14, further comprising a stepping motor to move one of the plurality of dispensing mechanisms,
   wherein the controller is further programmed to control the stepping motor to move a dispensing tube of the plurality of dispensing mechanisms without moving the reagent container holder.

22. A specimen analyzing apparatus for measuring a specimen by using a reagent, comprising:
   a plurality of dispensing mechanisms each of which includes a dispensing tube rotatably movable to a container removal area to suction and discharge a liquid;
   a reagent container holder in which the reagent can be added when the reagent container is placed in the reagent adding area;
   a receiving section to receive an addition command for an addition of the reagent;
   a reagent table on which the reagent container in the reagent container holder is placed and which is automatically movable relative to the container removal area; and
   a controller programmed to control movement of the reagent table and control the plurality of dispensing mechanisms to move each dispensing tube of the plurality of dispensing mechanisms thereby removing each dispensing tube of the plurality dispensing mechanisms from the reagent adding area when the receiving section receives the addition command.

23. The specimen analyzing apparatus according to claim 22, further comprising a stepping motor to move one of the plurality of dispensing mechanisms,
   wherein the controller is further programmed to control the stepping motor to move a dispensing tube of the plurality of dispensing mechanisms without moving the reagent container holder.

\* \* \* \* \*